US008992935B2

(12) United States Patent
Benghezal et al.

(10) Patent No.: US 8,992,935 B2
(45) Date of Patent: Mar. 31, 2015

(54) **MEANS OF CONTROLLING INFECTION PERSISTENCE OF *HELICOBACTER PYLORI***

(75) Inventors: Mohammed Benghezal, Scarborough (AU); Tobias Schoep, Coolbellup (AU); Alma Fulurija, White Gum Valley (AU); Douglas E. Berg, Cardiff by the Sea, CA (US); Barry J. Marshall, Subiaco (AU)

(73) Assignee: Ondek Pty. Ltd., Perth (AU)

(*) Notice: Subject to any disclaimer, the term of this patent is extended or adjusted under 35 U.S.C. 154(b) by 0 days.

(21) Appl. No.: 13/806,084

(22) PCT Filed: Jun. 24, 2011

(86) PCT No.: PCT/AU2011/000771

§ 371 (c)(1),
(2), (4) Date: Mar. 25, 2013

(87) PCT Pub. No.: WO2011/160182

PCT Pub. Date: Dec. 29, 2011

(65) Prior Publication Data

US 2013/0259888 A1 Oct. 3, 2013

(30) Foreign Application Priority Data

Jun. 25, 2010 (AU) ................................ 2010902818

(51) Int. Cl.

| | |
|---|---|
| ***C07K 14/195*** | (2006.01) |
| ***A61K 39/02*** | (2006.01) |
| ***C12N 1/36*** | (2006.01) |
| ***C12N 9/80*** | (2006.01) |
| *A61K 39/00* | (2006.01) |

(52) U.S. Cl.

CPC ................ *A61K 39/105* (2013.01); *C12N 1/36* (2013.01); *C12N 9/80* (2013.01); *C12Y 305/01005* (2013.01); *A61K 2039/522* (2013.01)

USPC .................. 424/190.1; 424/234.1; 424/200.1; 424/184.1; 435/252.3; 435/69.1; 435/69.3; 530/24; 530/387.3; 530/324

(58) Field of Classification Search

CPC ... A61K 2300/00; A61K 39/00; A61K 38/00; A61K 2039/51; A61K 2039/523; A61K 2039/02; A61K 38/164; A61K 35/74; A61K 2039/52; A61K 39/105; C07K 16/121; C07K 2319/00; C07K 14/195; G01N 33/56911; G01N 2333/195; C12Q 1/689; C12Q 1/58; C12N 1/00; C12N 15/74; C12N 1/04

USPC ........... 530/24, 387.3, 324; 424/190.1, 234.1, 424/200.1, 184.1, 203.1, 197.11, 93.2; 435/252.3, 69.1, 69.3, 12, 243

See application file for complete search history.

(56) References Cited

U.S. PATENT DOCUMENTS 5,843,460 A * 12/1998 Labigne et al. ............ 424/234.1
6,709,851 B1 3/2004 Soman et al.

FOREIGN PATENT DOCUMENTS

CN 1887349 A 1/2007
CN 1927394 A * 3/2007
EP 2082750 A1 * 7/2009
WO 96/34624 11/1996

OTHER PUBLICATIONS

Marshall et al. 2007 (*Helicobacter pylori* as a vaccine delivery system; *Helicobacter* 12(2):75-79).*
Svennerholm et al. 2008 (Vaccines against enterotoxigenic *Escherichia coli*; Expert Rev Vaccines 7(6):795-804).*
Ferrero et al., "Construction of isogenic urease-negative mutants of *Helicobacter pylori* by allelic exchange," J Bacteriology 174:4212-4217, 1992.
Genbank Accession No. AAD07143.1; 2 pages.
International Search Report for PCT application No. PCT/AU2011/000771, mailed Aug. 22, 2011, 5 pages.
International Preliminary Report on Patentability for PCT application No. PCT/AU2011/000771, mailed Oct. 5, 2011, 16 pages.
Marshall, et al., "*Helicobacter pylori* as a vaccine delivery system," *Helicobacter* 12(2):75-79, 2007.
Schoep, et al., "Properties of *Helicobacter pylori* urease complex are essential for persistence", PLoS ONE 5(11):e15402.doi:10.1371/journal.pone.0015042, (2010).
Nam-Chul et al., "Supramolecular assembly and acid resistance of *Helicobacter pylori* urease", Nature Structural Biology, 2001, 8(6):505-9.
Supplementary European Search Report dated Oct. 31, 2013 for EP 11797396.
First Office Action in related Chinese Application No. 201180041142.7.

* cited by examiner

*Primary Examiner* — J. Hines
*Assistant Examiner* — Mary Lyons
(74) *Attorney, Agent, or Firm* — Pepper Hamilton LLP

(57) ABSTRACT

The present invention relates to a means of controlling infection persistence of *Helicobacter pylori* (*H. pylori*). In particular, the present invention relates to an isolated, genetically modified *Helicobacter pylori* comprising a functional urease, wherein the contiguous amino acid sequence between amino acid 529 and amino acid 555 of SEQ ID NO:1 is altered to produce said modified *Helicobacter pylori* which is unable to establish or maintain a persistent infection.

10 Claims, 7 Drawing Sheets a b c d

```
                                        Site 8
                                          |
                     540        550        560
                  ....|....|....||....|....|....|....
      sp|P69996   IEVNPETERVFVDGKEVTSKPANKVSLAQLESIF
      sp|P42823   .......K.K...N....HA.D.L.....YNL.
      sp|Q93PJ4   .......E.R.NNYKI...VE.....G..YCL.
      tr|Q17YJ8   IF.D.KSFE..IE..LC.....SELP...RYFF.
      tr|Q4CHE3   ...D....E.K...EII.CE..RKVLPM..RYFL.
      sp|Q9KG59   ..ID....E.K...ENI.C..FEE.A...RYFL.
      sp|Q07397   .D.D.Q..E.K...QL..CE..EI.PM..RYFL.
      tr|Q1XLS1   .F....N.E.R...EKIICE..FHLPM..RYFL.
      sp|Q5KYM1   .D.D.Q..E.K...RLI.CE..EV.AM..RYFL.
      sp|Q5FB23   .....Q..E.KIN.ELIS..SVDSLA..RKYFMI
      tr|Q0VKY1   L..D.Q..E.RA..QLL..CE..EVLPM..RYFL.
      sp|Q733J6   ...D.Q..E.K...VI..CEAVDVLPM..RYFL.
      sp|Q2JQ88   .......E.RA..ELL..CE..EVLPM..RYFL.
      tr|Q4IXD2   ...D.Q..Q.KA..QLLNCE..EVLP...RYFL.
      tr|O52305   M..D.....RA..EMLVCE..FVLPM..RYFL.
      sp|Q21P94   M..D....E.RA..QLL..CE..EELPM..RYFL.
      sp|P73061   ...D....E.RA..ELL..CE..SVLPM..RYFL.
      sp|Q2SYF7   .S.D....D.VA..ALL..CE..AVLPM..RYFL.
      tr|Q1FX09   ...DAQ..E.RA..ELL..CE..FELP.F.RYCL.
      tr|Q05PQ2   .F.D...Q.IAN..ELL..CE..KVLPM..RYFL.
      tr|Q11EW4   ...D....E.RA..ELL..CE..TVLPM..RYFL.
      tr|Q0AC98   M..D....E.RA..ELLVCE..DVLPM..RYFL.
      tr|A0FWY4   .S.D...Q.IA...QLL..CE..KVLPM..RYFL.
      sp|Q8DMV6   ...D....E.RA..ELL..CE..TVLP...RYFL.
      sp|Q2SDQ1   M..DSQ..E.RAN.ELLVCE..KVLP...RYFL.
      sp|Q5LSQ2   .......E.RA..ELL..CQ..EVLPM..RYFL.
      tr|Q2BLC2   .F.D.Q..E.RA..ELL..CE..EELP....YTL.
      tr|Q161S8   .......E.RA..ELL..CQ..EVLPM..RYFL.
      sp|Q46IY3   ...D.Q..E..SN.ELL..CE..EVLP...RYLLL
      tr|O30337   VF.D...Q.VA..QLL..CE..TELPM..RYFL.
      sp|Q8XXT1   .T.D...Q.VA..MLL..CE..EVLPM..RYFL.
      sp|P77837   ..ID.K.Q..A..E.LSCQ.VDY.P.G.RYFL.
      sp|Q3KIT2   .D.D.Q..Q.KA..VLLNCE..EELPM..RYFL.
      tr|A0L6F2   M..D....E.RA..RLL..CE..TVLP...RYFL.
      sp|Q31B49   .S.D....E...S..ELL..CE..L.E.PM..RYFLL
      tr|Q9Z369   IF.D....E.F...EK..CE..EVLAM..RYFL.
      tr|Q1YUB5   ...DSQ..E.RA..QLINCE..FELPM..RYFL.
      tr|Q2ZGT0   ..IDYK.FE...N.RKINVP..VSLNSTRRYNL.
      tr|A0JRH4   .Q.D....K.F...ED..CE..DVLPM..RYFL.
      sp|Q7V1B6   .F.D.Q..E..A..VLLSCE.LEE.PM..KYFIL
      tr|Q0LFJ0   ...D....A.RA..ELL..CE..TSLP...RYFL.
      tr|Q1FJ39   .T.D.Q..D.R.N.ELI..CE..AELP...RYFL.
      sp|Q47G55   .T.D....V.KA..VHLVCE..FELP...RYFL.
      sp|Q8YQZ0   ...DS.S.E.RA..ELL..CE..FVLPM..RYFL.
      sp|Q9RYJ4   .Q......E.R.N.EL...CE.VDELP...KYFL.
      sp|Q3J770   ...D.QN.Q.RA..QLLNFE.SKVLPM..RYFL.
      tr|Q0FQX6   V......E.RNN.ELL..CE..FELPM..RYFLN
      sp|P42885   ...D....E.RA..ELL..CE..TVLPM..RYFL.
      sp|Q7V3V2   V..D.Q..E..A..DLL..CD..EELPM..RYLLL
```

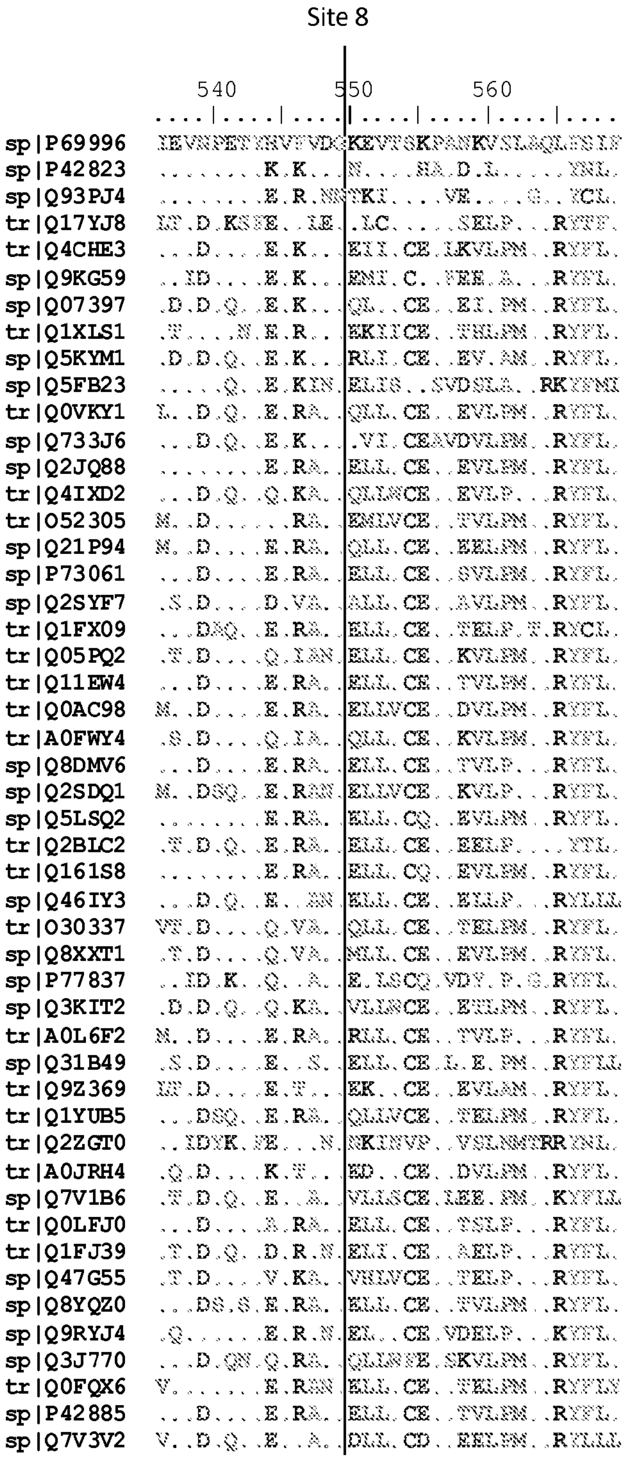

Figure 6

MEANS OF CONTROLLING INFECTION PERSISTENCE OF *HELICOBACTER PYLORI*

CROSS-REFERENCE TO RELATED APPLICATIONS

This application is a U.S. National Phase Application under 35 U.S.C. §371 of International Application PCT/AU2011/000771, filed on Jun. 24, 2011, which claims priority to AU Application No. 2010902818, filed on Jun. 25, 2010, the contents of each of which are hereby incorporated by reference in their entireties.

FIELD

The present invention relates to a means of controlling infection persistence of *Helicobacter pylori* (*H. pylori*). In particular, the present invention relates to *H. pylori* which has a modified urease, but is still capable of infection at a reduced persistence.

BACKGROUND

*Helicobacter pylori* chronically infects the gastric mucosa of billions of people worldwide, causes peptic ulcer disease in 10% or more of them, and is also implicated as an early critical risk factor for gastric cancer, one of the most frequently lethal malignancies in human populations (Suzuki et al., 2006, *Carcinogenesis*). However, the mechanisms by which *H. pylori* establishes and maintains colonization remains poorly understood. While these mechanisms remain poorly understood it is difficult to consider the development of useful vaccines against *H. pylori*. Moreover, the use of attenuated *H. pylori* as a biological delivery vehicle for peptides will remain elusive.

One of the first characterised factors essential for colonization by *H. pylori* was urease, an abundant enzyme that decreases the acidity of *H. pylori*'s immediate environment by generating ammonia and carbonate from the urea we secrete as metabolic waste (Marcus & Scott, 2001, *Helicobacter,* 6(2), 93-99; Hu & Mobley, 1990, *Infect. Immun.,* 58(4), 992-998). Although such local control of pH is considered essential, urease-negative *H. pylori* strains have been shown to be unable to colonise piglets whose acid secretion has been suppressed, suggesting an additional role for urease (Eaton & Krakowka, 1994, *Infect. Immun.,* 62(4), 992-998).

In order to produce a more effective vaccine strain of *H. pylori* or a strain that could be used as a biological vehicle the inventors have studied the dodecamer surface contribution to urease acid stability and host interactions of *H. pylori.*

SUMMARY

The inventors have shown that the region from about amino acid 529 to about amino acid 555 of UreB (GenBank AAD07143.1; SEQ ID NO:1) controls the ability of *Helicobacter pylori* to establish a persistent infection without affecting the urease activity.

Accordingly, in a first aspect the present invention provides an isolated, genetically modified *Helicobacter pylori* comprising a functional urease, wherein the contiguous amino acid sequence between amino acid 529 and amino acid 555 of SEQ ID NO:1 is altered to produce said modified *Helicobacter pylori* which is unable to establish or maintain a persistent infection.

In some embodiments, the amino acid sequence between amino acid 529 to amino acid 555 of SEQ ID NO:1 is altered by deletion, mutation or insertion. The alteration may comprise a conservative or non-conservative amino acid change.

In some embodiments, the amino acids that are altered are selected from the group consisting of 547, 548 and 549 of SEQ ID NO:1. Preferably, the amino acid alteration comprises an insertion of one or more amino acids in-frame into the contiguous amino acid sequence between amino acid 529 and amino acid 555 of SEQ ID NO:1.

In some embodiments, the insertion comprises between 10 and 100 amino acids. Preferably, between 10, 11, 12, 13, 14, 15, 16, 17, 18, 19, 20, 21, 22, 23, 24, 25, 26, 27, 28, 29, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 to 100 amino acids. Most preferably, between about 20 to about 50 amino acids.

In some embodiments, the genetically modified *Helicobacter pylori* of the present invention will further comprise one or more nucleic acid molecule(s) encoding at least one heterologous antigen or a functional fragment thereof. The nucleic acid molecule may reside extra-chromosomally or will preferably comprise an insertion into the contiguous amino acid sequence between amino acid 529 and amino acid 555 of SEQ ID NO:1. In some embodiments, the insertion is between amino acid 549 and 550.

In some embodiments, the heterologous antigen or a functional fragment thereof will be from a pathogenic microorganism. Preferably, the pathogenic microorganism will be selected from the group consisting of a virus, a bacterium, a protozoan and a fungus.

In some embodiments, the heterologous antigen is selected from the group consisting of a human immunodeficiency virus (HIV) antigen, an HTLV antigen, an SIV antigen, an RSV antigen, a PIV antigen, an HSV antigen, a CMV antigen, an Epstein-Barr virus antigen, a Varicella-Zoster virus antigen, a mumps virus antigen, a measles virus antigen, an influenza virus antigen, a poliovirus antigen, a rhinovirus antigen, a hepatitis A virus antigen, a hepatitis B virus antigen, a hepatitis C virus antigen, a Norwalk virus antigen, a togavirus antigen, an alphavirus antigen, a rubella virus antigen, a rabies virus antigen, a Marburg virus antigen, an Ebola virus antigen, a papilloma virus antigen, a polyoma virus antigen, a metapneumovirus antigen, a coronavirus antigen, a *Vibrio cholerae* antigen, a *Plasmodium falciparum* antigen, a *Plasmodium vivax* antigen, a *Plasmodium ovate* antigen, a *Plasmodium malariae* antigen, a *Plasmodium knowlesi* antigen, a *Streptococcus pneumoniae* antigen, *Streptococcus pyogenes* antigen, a *Helicobacter pylori* antigen, a *Streptococcus agalactiae* antigen, a *Neisseria meningitidis* antigen, a *Neisseria gonorrhoeae* antigen, a *Corynebacterium diphtheriae* antigen, a *Clostridium tetani* antigen, a *Bordetella pertussis* antigen, a *Haemophilus* antigen, a *Chlamydia* antigen and an *Escherichia coli* antigen.

In a second aspect, the present invention provides an immunogenic composition comprising an isolated, genetically modified *Helicobacter pylori* comprising a functional urease, wherein the contiguous amino acid sequence between amino acid 529 and amino acid 555 of SEQ ID NO:1 is altered to produce said modified *Helicobacter pylori* which is unable to establish a persistent infection and a pharmaceutically acceptable carrier.

In some embodiments, the immunogenic composition further comprises an adjuvant.

In a third aspect, the present invention provides a method for protecting a mammal against infection with a pathogenic microorganism comprising the step of administering an immunologically effective amount of an immunogenic composition comprising an isolated, genetically modified *Helicobacter pylori* comprising a functional urease, wherein the contiguous amino acid sequence between amino acid 529 and amino acid 555 of SEQ ID NO:1 is altered to produce said modified *Helicobacter pylori* which is unable to establish a persistent infection and a pharmaceutically acceptable carrier.

In a fourth aspect, the present invention provides a method of controlling the ability of *Helicobacter pylori* to establish a persistent infection comprising the step of altering the contiguous amino acid sequence between amino acid 529 and amino acid 555 of SEQ ID NO:1 to produce a modified UreB subunit of urease, wherein said urease retains de-acidification function, but said *Helicobacter pylori* is unable to establish a persistent infection.

In a fifth aspect, the present invention provides a method of vaccinating a mammal against *Helicobacter pylori* infection comprising the step of administering to said mammal an isolated, genetically modified *Helicobacter pylori* comprising a functional urease, wherein the contiguous amino acid sequence between amino acid 529 and amino acid 555 of SEQ ID NO:1 is altered to produce said modified *Helicobacter pylori* which is unable to establish a persistent infection.

In a sixth aspect, the present invention provides an immunogenic composition for use in vaccinating a mammal said composition comprising an isolated, genetically modified *Helicobacter pylori* comprising a functional urease, wherein the contiguous amino acid sequence between amino acid 529 and amino acid 555 of SEQ ID NO:1 is altered to produce said modified *Helicobacter pylori* which is unable to establish a persistent infection and a pharmaceutically acceptable carrier.

In some aspects, the heterologous antigen will reside in a plasmid vector comprising (a) a nucleotide sequence encoding the heterologous antigen and (b) a control or regulatory sequence operatively linked thereto which is capable of controlling the expression of the nucleotide sequence when the vector is transformed into the modified *Helicobacter pylori* of the present invention.

Non-limiting examples of a mammal included in the present invention are a primate, a canine, an equine, a bovine, a porcine, an ovine and a rodent.

The various delivery forms of the compositions are readily prepared for use in the practice of the present invention given the specific types and ratios of specific *Helicobacter pylori*, plasmid vectors and other delivery mechanisms described herein, and those formulation techniques known to those in the formulary arts, such as are described in Remington's Pharmaceutical Sciences, $20^{th}$ edition, Mack Publishing Company, which text is specifically incorporated herein by reference.

In a seventh aspect the present invention provides a method of preventing the persistence of *Helicobacter pylori* infection in a mammal comprising the step of administering to said mammal an agent capable of affecting the function of the contiguous amino acid sequence between amino acid 529 and amino acid 555 of SEQ ID NO:1.

BRIEF DESCRIPTION OF FIGURES

FIG. 6. Alignment showing conservation of ureases at region of site 8. Alignment of *H. pylori* UreB (sp|P69996; SEQ ID NO:23) at the region of site 8, for which the crystal structure has been determined (PDBe Entry: 1e9y), and ureases from different species. UniProtKB/Swiss-Prot numbers are displayed.

BRIEF DESCRIPTION OF THE SEQUENCES

Figure 1:
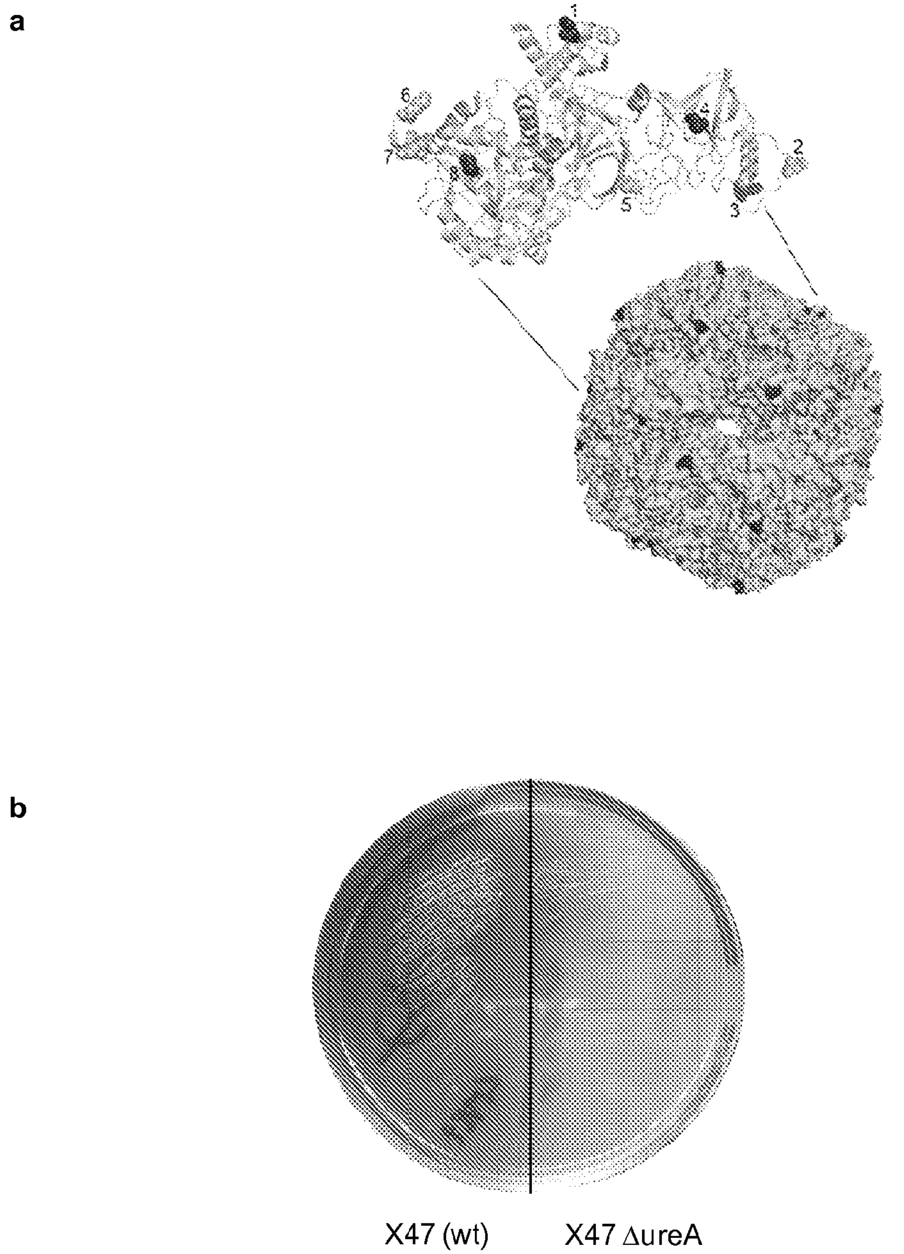
FIG. 1. Recombinant regions of urease and selection for enzyme function. a) Molecular structure of urease showing insertion sites on the surface of urease. Urease subunit A (green) and subunit B (blue) associate to form a dodecameric supramolecular molecule (Ha et al., 2001, *Nat Struct Biol,* 8(6), 505-509; Pinkse et al., *J Mass Spectrom.,* 38(3), 315-320). Insertion sites 1, 3, 4, and 8 are indicated in red. Urease activity could not be retained when altered at sites 2, 5, 6, and 7 (pink). b) Selection of bacteria producing functional urease on acidified media supplemented with the urease substrate, urea. The colour change observed on the left side indicated that bacterial colonies were producing functional urease and growing (X47 wild-type). Colour change did not occur on the right side, indicating that inoculated colonies were unable to grow as functional urease was not being produced (X47 ΔureA).

The following nucleic acid and amino acid sequences are referenced throughout the description of the present invention:

SEQ ID NO: 1—Amino acid sequence of the UreB subunit of the urease from *Helicobacter pylori* (GenBank AAD07143.1);

SEQ ID NO: 2—Nucleotide sequence encoding the UreB subunit of the urease from *Helicobacter pylori;*

SEQ ID NO: 3—Amino acid sequence of the UreA subunit of the urease from *Helicobacter pylori* (GenBank AAD07144.1);

SEQ ID NO: 4—Nucleotide sequence of the UreA subunit of the urease from *Helicobacter pylori;*

SEQ ID NO:5—Primer UF5-234

SEQ ID NO:6—Primer UR2-234

SEQ ID NO:7—Primer UR2-56

SEQ ID NO:8—Primer UF5-56

SEQ ID NO:9—Primer rpsL-F

SEQ ID NO:10—Primer ermR

SEQ ID NO:11—Primer silaF3

SEQ ID NO:12—Primer si3F3

SEQ ID NO:13—Primer si4F3

SEQ ID NO:14—Primer si8F3

SEQ ID NO:15—Primer HAFLAG

SEQ ID NO:16—Primer HAFLAG (rc)

SEQ ID NO:17—Primer UF1

SEQ ID NO:18—Primer UR6

SEQ ID NO:19—Primer si1aR1

SEQ ID NO:20—Primer si3R1

SEQ ID NO:21—Primer si4R1

SEQ ID NO:22—Primer si8R1

SEQ ID NO:23—Amino acids 535 to 575 of UreB (sp|P69996)

SEQ ID NO:24—Amino acids 535 to 575 of UreB (sp|P42823)

SEQ ID NO:25—Amino acids 535 to 575 of UreB (sp|Q93PJ4)

SEQ ID NO:26—Amino acids 535 to 575 of UreB (tr|Q17YJ8)

SEQ ID NO:27—Amino acids 535 to 575 of UreB (tr|Q4CHE3)

SEQ ID NO:28—Amino acids 535 to 575 of UreB (sp|Q9KG59)

SEQ ID NO:29—Amino acids 535 to 575 of UreB (sp|Q07397)

SEQ ID NO:30—Amino acids 535 to 575 of UreB (tr|Q1XLS1)

SEQ ID NO:31—Amino acids 535 to 575 of UreB (sp|Q5KYM1)

SEQ ID NO:32—Amino acids 535 to 575 of UreB (sp|QFB23)

SEQ ID NO:33—Amino acids 535 to 575 of UreB (tr|QVKY1)

SEQ ID NO:34—Amino acids 535 to 575 of UreB (sp|Q733J6)

SEQ ID NO:35—Amino acids 535 to 575 of UreB (sp|Q2JQ88)

SEQ ID NO:36—Amino acids 535 to 575 of UreB (tr|Q1XD2)

SEQ ID NO:37—Amino acids 535 to 575 of UreB (tr|052305)

SEQ ID NO:38—Amino acids 535 to 575 of UreB (sp|Q21P94)

SEQ ID NO:39—Amino acids 535 to 575 of UreB (sp|P73061)

SEQ ID NO:40—Amino acids 535 to 575 of UreB (sp|Q2SYF7)

SEQ ID NO:41—Amino acids 535 to 575 of UreB (tr|QFX09)

SEQ ID NO:42—Amino acids 535 to 575 of UreB (tr|Q05PQ2)

SEQ ID NO:43—Amino acids 535 to 575 of UreB (tr|Q1EW4)

SEQ ID NO:44—Amino acids 535 to 575 of UreB (tr|QOAC98)

SEQ ID NO:45—Amino acids 535 to 575 of UreB (tr|AOFWY4)

SEQ ID NO:46—Amino acids 535 to 575 of UreB (sp|Q8DMV6)

SEQ ID NO:47—Amino acids 535 to 575 of UreB (sp|Q2SDQ1)

SEQ ID NO:48—Amino acids 535 to 575 of UreB (sp|Q5LSQ2)

SEQ ID NO:49—Amino acids 535 to 575 of UreB (tr|Q2BLC2)

SEQ ID NO:50—Amino acids 535 to 575 of UreB (tr|Q161S8)

SEQ ID NO:51—Amino acids 535 to 575 of UreB (sp|Q61Y3)

SEQ ID NO:52—Amino acids 535 to 575 of UreB (tr|030337)

SEQ ID NO:53—Amino acids 535 to 575 of UreB (sp|Q8XXT1)

SEQ ID NO:54—Amino acids 535 to 575 of UreB (sp|P77837)

SEQ ID NO:55—Amino acids 535 to 575 of UreB (sp|Q3KIT2)

SEQ ID NO:56—Amino acids 535 to 575 of UreB (sp|A0L6F2)

SEQ ID NO:57—Amino acids 535 to 575 of UreB (sp|Q31B49)

SEQ ID NO:58—Amino acids 535 to 575 of UreB (sp|Q9Z369)

SEQ ID NO:59—Amino acids 535 to 575 of UreB (sp|Q1YUB5)

SEQ ID NO:60—Amino acids 535 to 575 of UreB (sp|Q2ZGT0)

SEQ ID NO:61—Amino acids 535 to 575 of UreB (sp|A0JRH4)

SEQ ID NO:62—Amino acids 535 to 575 of UreB (sp|Q7V1B6)

SEQ ID NO:63—Amino acids 535 to 575 of UreB (sp|Q0LFJ0)

SEQ ID NO:64—Amino acids 535 to 575 of UreB (sp|Q1FJ39)

SEQ ID NO:65—Amino acids 535 to 575 of UreB (sp|Q47G55)

SEQ ID NO:66—Amino acids 535 to 575 of UreB (sp|Q8YQZ0)

SEQ ID NO:67—Amino acids 535 to 575 of UreB (sp|Q9RYJ4)

SEQ ID NO:68—Amino acids 535 to 575 of UreB (sp|Q3J770)

SEQ ID NO:69—Amino acids 535 to 575 of UreB (tr|QFQX6)

SEQ ID NO:70—Amino acids 535 to 575 of UreB (sp|P42885)

SEQ ID NO:71—Amino acids 535 to 575 of UreB (sp|Q7V3V2)

Definition of Terms

As used herein, certain terms may have the following defined meanings. As used in the specification and claims, the singular forms "a", "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All strains *Helicobacter pylori* are included in the scope of the present application as long as they have a functional urease gene. Particularly preferred strains of *Helicobacter pylori* include strains deposited at the American Type Culture Collection (ATCC) as ATCC Accession Nos: 43504; 43504D-5; 43526; 43579; 43629; 49396; 49503; 51110; 49503; 51111; 51407; 51652; 51653; 51932; and 53727. Also see, for example, U.S. Pat. No. 5,459,041 incorporated herein by reference. Other preferred strains of *Helicobacter pylori* include strains deposited at the National Measurement Institute under Accession Nos. V09/009,101; V09/009,102; V09/009,103; V10/014,059; V10/014,060 and V09/009,104.

As used herein the term "isolated" is meant to describe a *Helicobacter pylori* cell, a polynucleotide or a polypeptide that is in an environment different from that in which the *Helicobacter pylori* cell, polynucleotide or polypeptide naturally occurs. An isolated genetically modified *Helicobacter pylori* cell may be present in a mixed population of *Helicobacter pylori* cells.

A "genetically modified" *Helicobacter pylori* refers to a *Helicobacter pylori* bacterium that differs in its pheno- and/or genotype from that of the corresponding wild type *Helicobacter pylori* in that it comprises an alteration to the urease gene present in *Helicobacter pylori*. On the one hand, the genetically modified *Helicobacter pylori* maintains urease activity, but on the other hand the factors required for establishing a persistent infection are 'knocked-out' or 'altered'. Methods for the genetic modification of the *Helicobacter pylori* are well-known in the art; cf. for example Sambrook, J. and Russell, D. W. (2001), "Molecular Cloning—A Laboratory Manual", Cold Spring Harbor Laboratory Press, New York, 3rd Edition.

Genes encoding urease of *Helicobacter pylori* have been described and sequenced (Labigne et al., (1991), *J. Bacteriol.*, 173: 1920-1931). Of the seven genes involved in urease expression and secretion, only two genes encode the two structural subunits urease A and B of the urease enzyme; ureA (SEQ ID NO:3) and ureB (SEQ ID NO:1). These two polypeptides form a polypeptide complex having urease activity.

Urease activity can be determined a number of ways. For example, it is known that urease converts urea into ammonium carbonate, which then decomposes into ammonia and carbon dioxide. Consequently, in the past, one test for detecting the presence of *Helicobacter pylori* included the steps of contacting a sample of gastric material with a composition containing urea and an indicator, namely a pH indicator that changes colour when there is a rise in pH. If urease is present within the gastric material it breaks down the urea, which results in the formation of ammonia after further decomposition and causes the pH indicator to change colour. *Helicobacter pylori* urease activity can also be detected by orally administering urea to a subject with subsequent monitoring of the exhaled dioxide and ammonia. Various test for urease activity are described in U.S. Pat. No. 4,748,113 and US Pat. Applic. No. 20030082664, which are incorporated herein by reference.

The term "functional fragment" when used herein with reference to urease, refers to any fragment of the *Helicobacter pylori* urease (i.e. a molecule which is reduced in size or truncated compared with the naturally occurring form) that still has the ability to convert urea into ammonium carbonate. Determination of the ability of the urease or functional fragment thereof to convert urea into ammonium carbonate may in this connection take place both qualitatively and quantitatively (i.e. as a quantifiable measurement).

The term "nucleic acid" used herein refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Percent identity (homology)" of two amino acid sequences or of two nucleic acids is determined using the algorithm of Karlin and Altschul, 1990, *Proc. Natl. Acad. Sci. USA,* 87:2264-2268, 1990, modified as in Karlin and Altschul (*Proc. Natl. Acad. Sci. USA* 90:5873-5877, 1993). Such an algorithm is incorporated into the NBLAST and XBLAST programs of Altschul et al. (*J. Mol. Biol.* 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (eg., SEQ ID NO: 2). To obtain gapped alignments for comparison purposes, Gapped BLAST is utilised as described in Altschul et al. (*Nucleic Acids Res.* 25:3389-3402, 1997). When utilising BLAST and Gapped BLAST programs, the default parameters of the respective programs (eg., XBLAST and NBLAST) are used. These maybe found on the World Wide Web at the URL "ncbi.nim.nih.gov."

As used herein, the term "exogenous nucleic acid" refers to a nucleic acid that is not normally or naturally found in and/or produced by *Helicobacter pylori* in nature. As used herein, the term "endogenous nucleic acid" refers to a nucleic acid that is normally found in and/or produced by *Helicobacter pylori* in nature. An "endogenous nucleic acid" is also referred to as a "native nucleic acid" or a nucleic acid that is "native" to *Helicobacter pylori.*

The term "heterologous nucleic acid," as used herein, refers to a nucleic acid wherein at least one of the following is true: (a) the nucleic acid is foreign ("exogenous") to (i.e., not naturally found in) *Helicobacter pylori*; (b) the nucleic acid comprises a nucleotide sequence that is naturally found in (e.g., is "endogenous to") *Helicobacter pylori* (e.g., the nucleic acid comprises a nucleotide sequence that is endogenous to *Helicobacter pylori*) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms.

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a *Helicobacter pylori* cell.

The term "transformation" is used interchangeably herein with "genetic modification" and refers to a permanent or transient genetic change induced in a *Helicobacter pylori* cell following introduction of new nucleic acid. Genetic change ("modification") can be accomplished either by incorporation of the new DNA into the urease gene of the *Helicobacter pylori* cell, or by transient or stable maintenance of the new DNA as an episomal element such as a plasmid or expression vector, which may contain one or more selectable markers to aid in their maintenance in the recombinant *Helicobacter pylori* cell. Suitable methods of genetic modification include transfection, conjugation, protoplast fusion, electroporation, particle gun technology, calcium phosphate precipitation, direct microinjection, and the like. A general discussion of these methods can be found in Ausubel, et al, Short Protocols in Molecular Biology, 3$^{rd}$ ed., Wiley & Sons, 1995.

"Transforming nucleic acid sequence" as used herein means a plasmid vector, or other expression cassette containing a nucleic acid sequence encoding a an antigen. In some embodiments of the present invention the nucleic acid sequence can encode for one or more antigens.

"Transforming nucleic acid sequence" can also be used to mean a "transgene" in accordance with certain embodiments of the present invention. In another embodiment of the present invention the transforming nucleic acid sequence includes nucleic acid sequence encoding for a promoter and/or other regulatory elements.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

The genetically modified *H. pylori* of the present invention is incapable of establishing or maintaining a persistent infection. A "persistent infection" is an infection in which *H. pylori* is not cleared or eliminated from the infected mammal, even after the induction of an immune response. Persistent infections can be chronic infections or latent infections. Latent infection is characterized by the lack of demonstrable infectious *H. pylori*. Chronic infection is characterized by the continued presence of the *H. pylori* following the primary infection. While acute infections are relatively brief (lasting a few days to a few weeks) and resolved from the body by the immune system, persistent infections can last for example, for months, years, or even a lifetime. These infections may also recur frequently over a long period of time, involving stages of silent and productive infection without cell killing or even producing excessive damage to the host cells. Persistent infections often involve stages of both silent and productive infection without rapidly killing or even producing excessive damage of the host cells. It is usually considered that the acute phase for *H. pylori* infection lasts for about 10-14 days and a chronic infection is established after about three months leading to a lifelong colonisation or persistence. Thus, in the present invention the genetically modified *H. pylori* of the present invention is capable of establishing an initial infection, but this infection is not maintained for more than about 12, 11, 10, 9, 8, 7, 6, 5, 4, 3 or 2 months as compared to an infection with a wild type *Helicobacter pylori* which can remain lifelong.

A "vaccine composition", "vaccine", "immunogenic composition", and similar terms refer to a composition comprising a strain of live genetically modified *Helicobacter pylori* that expresses at least one antigen, such that when administered to a mammal, the bacteria will elicit an immune response in the mammal against the antigen(s) expressed in the *Helicobacter pylori* and, thereby, provide at least partial protective immunity against organism from which the antigen was isolated. Such protective immunity may be evidenced by any of a variety of observable or detectable conditions, including but not limited to, diminution of one or more disease symptoms, shorter duration of illness, diminution of tissue damage, regeneration of healthy tissue, clearance of pathogenic microorganisms from the mammal, and increased sense of well being by the mammal. Although highly desired, it is understood by persons skilled in the art that no vaccine is expected to induce complete protection from a disease in every individual that is administered the vaccine or that protective immunity is expected to last throughout the lifetime of an individual without periodic "booster" administrations of a vaccine composition. It is also understood that a live vaccine comprising a genetically modified *Helicobacter pylori* described herein may be, at the discretion of a healthcare professional, administered to an individual who has not presented symptoms of disease, but is considered to be at risk of infection or is known to already have been exposed to a disease, e.g., by proximity or contact with infected mammals or contaminated air, liquids, or surfaces.

A "therapeutically effective amount" of a genetically modified *Helicobacter pylori* of the present invention or an antigen expressed by said *H. pylori* as described herein is understood to comprise an amount effective to elicit the desired response but insufficient to cause a toxic reaction. A desired response, for example, may constitute the formation of a sufficient and/or acceptable detectable antibody titer level in a blood sample. The dosage and duration of treatment of the preparation to be administered to a mammal will be determined by the health professional attending the mammalian subject in need of treatment, and will consider the age, sex and weight of the subject, and the specific *Helicobacter pylori* and nucleic acid molecule being expressed.

The terms "oral", "enteral", "enterally", "orally", "non-parenteral", "non-parenterally", and the like, refer to administration of a genetically modified *Helicobacter pylori* of the present invention to a mammal by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "inducing immune tolerance to an antigen," comprises mucosal delivery of an antigen by an isolated, genetically modified *Helicobacter pylori* secreting an antigen for the preparation of a medicament, medical food or nutraceutical for mucosal delivery to treat an immune response related disease in a mammal, wherein said antigen is preferably continuously present in said mammal.

A "heterologous" antigen is one not native to *Helicobacter pylori*, i.e., not expressed by *Helicobacter pylori* in nature or prior to introduction into *Helicobacter pylori*.

"Detectable immune response" as used herein is either an antibody (humoral) or cytotoxic (cellular) response formed in a mammal in response to an antigen that can be measured using routine laboratory methods including, but not limited to enzyme-linked immunosorbant assays (ELISA), radio-immune assays (RIA), Enzyme-linked ImmunoSPOT (ELISPOT), immunofluorescent assays (IFA), complement fixation assays (CF), Western Blot (WB) or an equivalent thereto.

DESCRIPTION OF THE PREFERRED EMBODIMENTS

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety.

However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional techniques of pharmacology, molecular biology (including recombinant techniques), cell biology, biochemistry, and immunology, which are within the skill of the art. Such techniques are well known to the skilled worker, and are explained fully in the literature. See, eg., Coligan et al. "Current protocols in Protein Science"

(1999) Volume I and II (John Wiley & Sons Inc.); Sambrook et al., (Molecular Cloning: A Laboratory Manual, $2^{nd}$ & $3^{rd}$ Editions, Cold Spring Harbor Laboratory press (1989) (2001); and Bailey, J. E. and Ollis, D. F., Biochemical Engineering Fundamentals, McGraw-Hill Book Company, NY, 1986; "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

In the broadest aspect, the present invention provides an isolated, genetically modified *Helicobacter pylori*. In some embodiments, the *Helicobacter pylori* is initially isolated from clinical samples taken from a mammalian subject which is chronically infected with *H. pylori*. The urease ureB gene (SEQ ID NO:1) is then modified by deletion, mutation or insertion such that the urease remains functional ie capable of converting urea into ammonium carbonate, which then decomposes into ammonia and carbon dioxide.

The region of the urease that is modified is from about amino acid 529 to about amino acid 555 of UreB (GenBank AAD07143.1; SEQ ID NO:1). In some embodiments, the region is between 529, 530, 531, 532, 533, 534, 535, 536, 537, 538, 539, 540, 541, 542, 543, 544, 545, 546, 547, 548, 549, 550, 551, 552, 553, 554 and 555. In some embodiments, the amino acids that are altered are selected from the group consisting of 547, 548 and 549 of SEQ ID NO:1.

The alterations can be made using methods known in the art such as oligonucleotide-mediated (site-directed) mutagenesis, alanine scanning, and PCR mutagenesis. Site-directed mutagenesis (Carter et al., (1986), *Nucl. Acids Res.,* 13:4331; Zoller et al., (1987), *Nucl. Acids Res.,* 10:6487), cassette mutagenesis (Wells et al., (1985), *Gene,* 34:315), restriction selection mutagenesis (Wells et al., (1986), *Philos. Trans. R. Soc. London SerA,* 317:415) or other known techniques can be performed on cloned DNA to produce an urease variant DNA.

In some embodiments, genomic DNA obtained from an isolate of *Helicobacter pylori* is inserted into a suitable shuttle vector, e.g., a shuttle plasmid with selectable markers, e.g., antibiotic markers, to assess their transformability. Broadly, a suitable shuttle vector will include one, two, three or more of the following features, a cloning site, a *Helicobacter pylori* origin of replication, an *E. coli* origin of replication, and an antibiotic resistance gene and/or selectable marker. Art-known vectors suitable for this purpose, or readily adaptable for this purpose include, for example, the recombinant shuttle plasmid pHR106 described by Roberts et al. (*Appl Env Mircobiol.,* 54: 268-270 (1988)); the PJIR 750 and PJIR 751 plasmids described by Bannam et al. (*Plasmid,* 29:233-235 (1993)); the promoterless PPSV promoter selection vector of Matsushita et al. (Plasmid, 31, 317-319 (1994)); the shuttle plasmids pJIR1456 and pJIR1457, described by Lyras et al. (*Plasmid,* 39, 160-164 (1988)); and the pAK201 shuttle vector described by Kim et al. (*Appl Environ Microbiol.,* 55, 360-365 (1989)), the contents of which are incorporated herein by reference in their entireties. Removal of the *Helicobacter pylori* origin of replication converts the shuttle vector into a suicide vector.

Alternatively, homologous recombination can be used to introduce a mutation or exogenous sequence into the urease gene.

Once the alteration has been made then nucleic acid transfer protocols are used including transformation/transfection, electroporation, liposome mediated nucleic acid transfer, N-[1-(2,3-Dioloyloxy)propyl]-N,N,N-trimethylammonium methylsulfate meditated transformation, and others. One skilled in the art will be readily able to select the appropriate tools and methods for genetic modifications of the *Helicobacter pylori* according to the knowledge in the art and design choice.

In some embodiments, the present invention is directed at mucosal delivery of an immune dominant antigen secreted by the isolated, genetically modified *Helicobacter pylori* of the present invention. The purpose of the delivery is the suppression of local and systemic T-cell responses. This approach of antigen-delivery has the capacity for potentiating oral tolerance even in the setting of established hypersensitivity. Thus it is applicable for the prevention of disease caused by pathogens (ie vaccination) but also the treatment of autoimmune and/or allergic diseases.

Accordingly, in some embodiments, the amino acid alteration comprises an insertion of one or more amino acids in-frame into the contiguous amino acid sequence between amino acid 529 and amino acid 555 of SEQ ID NO:1, which encode one or more antigens or a functional fragments thereof. Preferably the insertion is between amino acid 549 and 550.

In some embodiments, the insertion will comprise between 10 and 100 amino acids. Preferably, between about 20 to about 50 amino acids.

In some embodiments, the heterologous antigen or a functional fragment thereof will be from a pathogenic microorganism. Preferably, the pathogenic microorganism will be selected from the group consisting of a virus, a bacterium, a protozoan and a fungus.

In some embodiments, the heterologous antigen is selected from the group consisting of a human immunodeficiency virus (HIV) antigen, an HTLV antigen, an SIV antigen, an RSV antigen, a PIV antigen, an HSV antigen, a CMV antigen, an Epstein-Barr virus antigen, a Varicella-Zoster virus antigen, a mumps virus antigen, a measles virus antigen, an influenza virus antigen, a poliovirus antigen, a rhinovirus antigen, a hepatitis A virus antigen, a hepatitis B virus antigen, a hepatitis C virus antigen, a Norwalk virus antigen, a togavirus antigen, an alphavirus antigen, a rubella virus antigen, a rabies virus antigen, a Marburg virus antigen, an Ebola virus antigen, a papilloma virus antigen, a polyoma virus antigen, a metapneumovirus antigen, a coronavirus antigen, a *Vibrio cholerae* antigen, a *Plasmodium falciparum* antigen, a *Plasmodium vivax* antigen, a *Plasmodium ovate* antigen, a *Plasmodium malariae* antigen, a *Plasmodium knowlesi* antigen, a *Streptococcus pneumoniae* antigen, *Streptococcus pyogenes* antigen, a *Helicobacter pylori* antigen, a *Streptococcus agalactiae* antigen, a *Neisseria meningitidis* antigen, a *Neisseria gonorrhoeae* antigen, a *Corynebacterium diphtheriae* antigen, a *Clostridium tetani* antigen, a *Bordetella pertussis* antigen, a *Haemophilus* antigen, a *Chlamydia* antigen and an *Escherichia coli* antigen.

Preferably, the antigen is displayed at the surface of the *Helicobacter pylori* or is secreted.

In one aspect of the invention there is provided a method for inducing immune tolerance to an antigen, comprising mucosal delivery of said antigen by an isolated, genetically modified *Helicobacter pylori* secreting an antigen for the preparation of a medicament, medical food or nutraceutical for mucosal delivery to treat an immune response related disease in a mammal, wherein said antigen is preferably continuously present in said mammal.

Preferably, the immune tolerance is induced in a mammal selected from the group consisting of a dog, a cat, a mouse, a rat, a pig, a cow, a sheep, a horse and a human. Preferably, the mammal is human. Preferably, the immune tolerance is mucosal tolerance.

Mucosa as used here can be any mucosa such as oral mucosa, rectal mucosa, urethral mucosa, vaginal mucosa, ocular mucosa, buccal mucosa, pulmonary mucosa and nasal mucosa. Mucosal delivery as used throughout the application encompasses the delivery to the mucosa. Oral mucosal delivery includes buccal, sublingual and gingival routes of delivery. Accordingly, the present invention relates to method in which said mucosal delivery is chosen from the group consisting of rectal delivery, buccal delivery, pulmonary delivery, ocular delivery, nasal delivery, vaginal delivery and oral delivery. Preferably, said mucosal delivery is oral delivery and said tolerance is oral tolerance.

Mucosal tolerance as used here throughout the application is the inhibition of specific immune responsiveness to an antigen in a mammal (including humans), after that said mammal has been exposed to said antigen via the mucosal route. Preferably, said mucosal tolerance is systemic tolerance. The subsequent exposure of the antigen can be every exposure known to the person skilled in the art, such as exposure by parenteral injection, by mucosal delivery, or by endogenous production such as in the case of auto-antigens. Oral tolerance is the inhibition of specific immune responsiveness to an antigen in a mammal (including humans), after that mammal has been exposed to said antigen via the oral route.

The present invention also relates to a method or use as described herein, wherein said induction of immune tolerance is at least 1.5, preferably 2, more preferably 3 times or more relative to before said induction. Alternatively, said antigen is tolerated at least 1.5, 2, 3 times or more relative to before said induction. The induction of immune tolerance can be measured by methods known in the art. Preferably, said induction of immune tolerance can be measured by modulation of a cytokine level in said animal. As such, the modulation can be an increase of a cytokine level, for instance said increase of a cytokine level is at least 1.5, 2, 3 times or more relative to before said induction, e.g. IL-10 or TGF-beta. Alternatively, said modulation is a decrease of the level of a particular cytokine level, for instance said decrease of the cytokine level is at least 1.5, 2, 3 times or more relative to before said induction, e.g. IL-12, IL-17 and IFN-gamma. The cytokines which are modulated may be chosen from any relevant cytokines, preferably said cytokines are chosen from the group consisting of IL-2, IL-4, IL-5, IL-6, IL-10, IL-12, IL-13, IL-17, IL-23, TNF-alpha, IFN-gamma, IFN-alpha, MCP-1, TGF-beta, RANK-L and Flt3L.

The invention will now be further described by reference only to the following non-limiting examples. It should be understood, however, that the examples following are illustrative, and should not be taken in any way as a restriction on the generality of the invention described herein.

EXAMPLE 1

Mutation by Insertion

To test the possible involvement of the urease surface in host-pathogen interactions, the UreA/UreB structure (Ha et al., 2001, supra) was analysed in silico to identify surface regions that might tolerate the insertion of two epitope tags (FIG. 1*a*).

Mutant *H. pylori* strains were then produced by chromosomal replacement of wild-type ureA or ureB gene DNAs with mutant DNAs with in-frame insertions encoding tag sequences flanked by semi-random six amino acid linkers at eight sites in the urease (FIG. 4) using standard PCR techniques.

Briefly, all PCR constructions used 26695 genomic DNA as template for initial amplifications. Primers used in this study are shown in Table 1 and the combinations used are shown in Table 2. The principles of splicing by overlap PCR have been previously reported (Shevchuk et al., 2004, *Nucleic Acid Res.,* 32(2), e19. To construct rpsL.ermB cassette (Dailidiene et al., 2006, *Appl. Environ. Microbiol.,* 72(9), 5908-5914) flanked by regions for homologous recombination 3 stages of PCR were

TABLE 1

SEQUENCES OF OLIGONUCLEOTIDES USED IN THIS STUDY

| Primer | Sequence (5' - 3') | SEQ ID NO: |
|---|---|---|
| UF5-234 | gtgtttaatccatagttataaagcatcccattggcctcaataggggtat | SEQ ID NO: 5 |
| UR2-234 | ttcaatagctataaattatttaataagtaacggtggcggtaaaaccct | SEQ ID NO: 6 |
| UR2-56 | ttcaatagctataaattatttaataagtaagtgagcttggcgcaactcttta | SEQ ID NO: 7 |
| UF5-56 | gtgtttaatccatagttataaagcatcgtgagcggtagtgtcgttgaat | SEQ ID NO: 8 |
| rpsL-F | gatgctttataactatggattaaacac | SEQ ID NO: 9 |
| ermR | ttacttattaaataatttatagctattgaa | SEQ ID NO: 10 |
| si1aF3 | ggcccttctttaggaaaaatttcaaatctttcaaagctvnnvnnvnnvnnvnnvnnggcctcaata ggggtatgcacggtt | SEQ ID NO: 11 |
| si3F3 | ggcccttctttaggaaaaatttcaaatctttcaaagctvnnvnnvnnvvvvnnvnnctccttaatt gtttttacatagttgt | SEQ ID NO: 12 |
| si4F3 | ggcccttctttaggaaaaatttcaaatctttcaaagctcatttcttactccttaattgtttttaca | SEQ ID NO: 13 |
| si8F3 | ggcccttctttaggaaaaatttcaaatctttcaaagctvnnvnnvnnvnnvnnvnngccatccacg aacacatggtaagtt | SEQ ID NO: 14 |

TABLE 1-continued

| SEQUENCES OF OLIGONUCLEOTIDES USED IN THIS STUDY | | |
|---|---|---|
| Primer | Sequence (5' - 3') | SEQ ID NO: |
| HAFLAG | tttatcatcgtcatctttataatctaagctaggcccaggatagctcccttctttttcggttaacca taagctaggcccttctttaggaaaaatttcaaat | SEQ ID NO: 15 |
| HAFLAG (rc) | atttgaaatttttcctaaagaagggcctagcttatggttaaccgaaaaagaagggagctatcctgg gcctagcttagattataaagatgacgatgataaa | SEQ ID NO: 16 |
| UF1 | cgactttggttaacccgcaaatcccat | SEQ ID NO: 17 |
| UR6 | gggcgtggtggattatgtgtatta | SEQ ID NO: 18 |
| si1aR1 | gattataaagatgacgatgataaannbnnbnnbnnbnnbnnbaatggtaaattagttcctggtga | SEQ ID NO: 19 |
| si3R1 | tttatcatcgtcatctttataatcvnnvnnvnnvnnvnnctccttaattgtttttacatagttgt | SEQ ID NO: 20 |
| si4R1 | gattataaagatgacgatgataaannbnnbnnbnnbnnbnnbaaaaagattagcagaaaagaatatgtt | SEQ ID NO: 21 |
| si8R1 | gattataaagatgacgatgataaannbnnbnnbnnbnnbnnbaaagaagtaacttctaaaccagcca | SEQ ID NO: 22 |

TABLE 2

PRIMER COMBINATIONS USED TO PRODUCE MODIFIED DNA

| Description | Stage | Product | Primer 1 | Primer 2 | Template |
|---|---|---|---|---|---|
| rpsL.ermB | 1 | A | UF1 | UR2-234 | genomic |
| site 1 | 1 | B | rpsL-F | ermR | genomic* |
| | 1 | C | UF5-234 | UR6 | genomic |
| | 2 | Fusion | UF1 | ermR | A + B |
| | 2 | Fusion | rpsL-F | UR6 | B + C |
| | 3 | Fusion | UF1 | UR6 | AB + BC |
| rpsL.ermB | 1 | A | UF1 | UR2-56 | genomic |
| site 8 | 1 | B | rpsL-F | ermR | genomic* |
| | 1 | C | UF5-56UR6 | UR6 | genomic |
| | 2 | Fusion | UF1 | ermR | A + B |
| | 2 | Fusion | rpsL-F | UR6 | B + C |
| | 3 | Fusion | UF1 | UR6 | AB + BC |
| Site 1 | 1 | A1 | UF1 | Si1aR1 | genomic |
| | 2 | A2 | UF1 | HAFLAG (rc) | A1 |
| | 1 | B1 | Si1aF3 | UR6 | genomic |
| | 2 | B2 | HAFLAG | UR6 | B1 |
| | 3 | Fusion | UF1 | UR6 | A2 + B2 |
| Site 3 | 1 | A1 | UF1 | Si3R1 | genomic |
| | 2 | A2 | UF1 | HAFLAG (rc) | A1 |
| | 1 | B1 | Si3F3 | UR6 | genomic |
| | 2 | B2 | HAFLAG | UR6 | B1 |
| | 3 | Fusion | UF1 | UR6 | A2 + B2 |
| Site 4 | 1 | A1 | UF1 | Si4R1 | genomic |
| | 2 | A2 | UF1 | HAFLAG (rc) | A1 |
| | 1 | B1 | Si4F3 | UR6 | genomic |
| | 2 | B2 | HAFLAG | UR6 | B1 |
| | 3 | Fusion | UF1 | UR6 | A2 + B2 |
| Site 8 | 1 | A1 | UF1 | Si8R1 | genomic |
| | 2 | A2 | UF1 | HAFLAG (rc) | A1 |
| | 1 | B1 | Si8F3 | UR6 | genomic |
| | 2 | B2 | HAFLAG | UR6 | B1 |
| | 3 | Fusion | UF1 | UR6 | A2 + B2 |

*Genomic DNA from X47 harbouring rpsL.ermB at the mdaB locus performed. Stage 1 involved the amplification of the rspL.ermB cassette, and flanking regions for homologous recombination at the urease locus. Stage 2 involved the addition of either flanking region to the rpsL.ermB cassette using 2 way SOE PCR, Stage 3 involved using these products as template to add both flanking regions to the rpsL.ermB cassette using 2 way SOE PCR (Table 2). To produce DNA encoding HA (aa 150-159 and aa 110-120 of Influenza virus A/PR/8/34 hemagglutinin protein; Casares et al., 1997, *Viral Immunol.,* 10(3), 129-136) and FLAG (DYKDDDDK) epitopes separated by a four amino acid linker, flanked by semi-random six amino acid linkers and regions for homologous recombination, 3 stages of PCR were performed using AccuPrime™ Pfx Supermix (Invitrogen). Stage 1 involved the addition of flanking linkers, stage 2 involved the addition of HA and FLAG epitopes, stage 3 involved the addition of flanking regions for homologous recombination using 2-way SOE PCR (Table 2). Thermocycling conditions were as follows: 94° C. for 15 s, 56° C. for 20 s, 68° C. for 3.5 min (10 cycles). After the addition of primers an additional 35 cycles of 94° C. for 15 s, 62° C. for 20 s, 68° C. for 3.5 min were performed, followed by a final extension of 3 min. Extension times were varied according to PCR product lengths.

Streptomycin resistant *H. pylori* strain X47 was used for all experiments (Kleanthous et al., 1995, *Gut,* 37, A94. Bacteria were grown on Brain Heart Infusion (BHI) based agar plates supplemented with 5% horse blood and when appropriate, with erythromycin (10 μg/mL) or streptomycin (10 μg/mL) in an atmosphere containing 5% $CO_2$.

Overnight cultures of *H. pylori* grown on BHI based agar plates were subcultured onto plates supplemented with DENT (Oxoid) in lawns of approximately 2 cm in diameter. PCR products were DpnI treated to remove residual genomic DNA and purified QIAQuick PCR Purification Kit (Quiagen) prior for use in transformation. Transformation was performed by the addition of approximately 1 μg of purified PCR product after growth of bacterial lawns for 6-8 hrs. After overnight incubation putative transformants were streaked on selective media.

Figure 2:
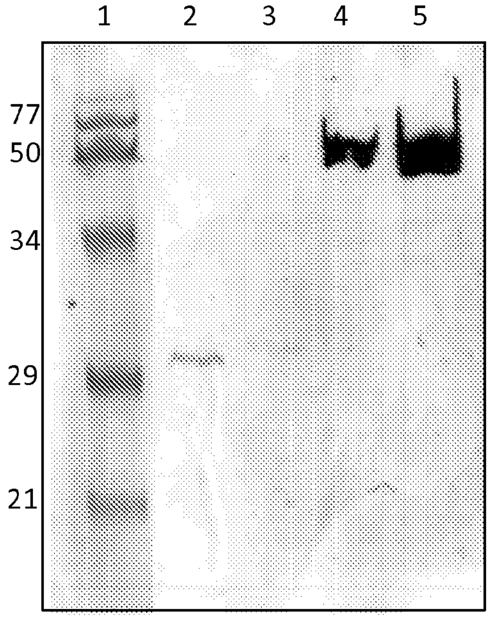
FIG. 2. Recombinant urease activity and acid stability. a) Western Blot analysis of *H. pylori* producing urease recombinant at sites 1, 3, 4 or 8. Lanes 1: Maker (MW: KDa shown); Lane 2: X47 (site 1); Lane 3: X47 (site 3); Lane 4: X47 (site 4); Lane 5: X47 (site 8). Recombinant urease was detected using anti-FLAG antibody directed against UreA (lanes 2 and 3) or UreB (lanes 4 and 5). b) Ability of permeabilised bacteria expressing wild-type or recombinant urease to neutralize acid after incubation at pH 3 in the presence of urea. To determine acid stability and activity of wild-type and recombinant ureases bacteria were incubated at pH 3 for 0, 2 or 10 min prior to assay of urease activity. After pre-incubation pH was neutralized, urea added as substrate and urease activity at was measured by a change in pH as indicated by a change in the colour of phenol red. Significantly reduced urease activities independent of pre-incubation at pH 3 are annotated "*" (Student's T-test, 2 tailed, equal variance). SEM displayed (n=3).
Figure 2:
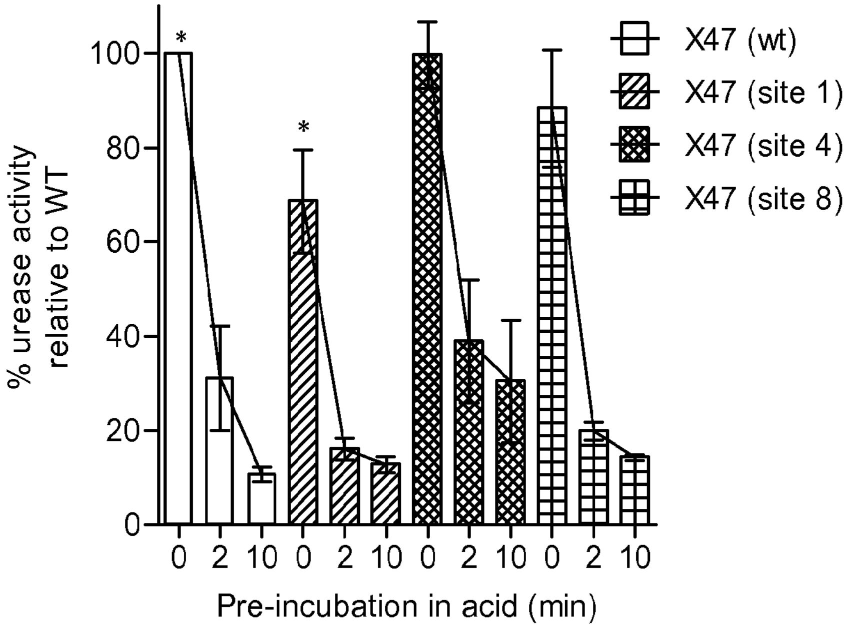

*H. pylori* producing functional urease were selected on BHI based agar plates supplemented with 7% (v/v) horse serum, phenol red (100 mg/L), and urea (600 mg/L). Media was acidified to pH 3 using 1M HCl to select for *H. pylori* producing functional urease, as illustrated in FIG. 2.

Four of eight candidate sites yielded mutant urease enzymes that allowed *H. pylori* to grow and metabolize urea (FIG. 1*b*). Insertions at the remaining four sites did not result in isolation of bacteria expressing functional ureases under these conditions.

*H. pylori* were harvested from mouse stomachs, grown for 4 d, harvested and resuspended in SDS-PAGE loading buffer. Standard SDS-PAGE and Western Blot methodologies were performed (Sambrook & Russell, 2001, Molecular Cloning, supra). Electrophoresis was performed using SDS-PAGE on a discontinuous 10% gel. For Western Blotting proteins were transferred to PVDF Immuno-Blot PVDF (0.2 μM) membrane (Biorad). Membranes were blocked overnight at 2% Blocking Reagent (Roche) in Maleic acid buffer (100 mM Maleic acid, 150 mM NaCl, pH 7.5, 20° C.) supplemented with 0.2% (v/v) Tween 20. To detect FLAG membranes were probed with a 1:1000 dilution of monoclonal anti-FLAG (Sigma Aldrich) in 1% Blocking Reagent supplemented with 0.1% (v/v) Tween 20 for 2 hours at room temperature. For detection membranes were incubated with rabbit anti-mouse IgG conjugated to horse radish peroxidase (Jackson ImmunoResearch Laboratories, Inc.) under identical conditions for 1 h at room temperature. Detection was performed using Chemiluminescent Peroxidase Substrate-3 (Sigma-Aldrich) and the FujiFilm LAS-3000 Imager. Urease was similarly probed using a 1:200 dilution anti-urease alpha subunit (bc-14; Santa Cruz Biotechnology) and detected using a 1:2500 dilution of rabbit anti-goat HRP conjugate antibody (Jackson ImmunoResearch Laboratories, Inc.).

Western blot analysis confirmed that *H. pylori* producing recombinant urease at sites 1, 3, 4 or 8 contained insertions of epitope tags (FIG. 2*a*). The pH of the mouse stomach lumen, which *H. pylori* must traverse to establish gastric mucosal infection is between 3 and 4 (McConnell et al., (2008), *J Pharm Pharmacol.,* 60 (1), 63-70). To determine if these insertions in urease's surface exposed loops altered its activity or stability we assayed enzymatic activity in bacteria expressing wild-type or mutant urease after exposure to acid (pH 3). One of the mutant ureases (insertion at site 1) was more sensitive than wild type, and the three other mutant ureases were similar to wild type in their sensitivity to this acid treatment (FIG. 2*b*; Student's T-test; $p<0.05$).

EXAMPLE 2

Experimental Infection of Mice

C57BL/6, *Helicobacter* free, mice were purchased from the Animal Resource Centre (Perth, Western Australia). Studies were performed with approval from the UWA Animal Ethic Committee (approval No. 07/100/598). Eight week old mice were orogastrically inoculated with approximately $1.0\times10^9$ *H. pylori* harvested from an overnight agar plate based culture into BHI broth (Oxoid). Mice were inoculated with pools of 3 independent, genetically characterised clones expressing wild type or recombinant urease. To determine the level of colonisation, stomachs were harvested from sacrificed animals, opened, and residual food removed. Opened stomachs were suspended in 500 μL PBS and homogenised using 5 mm stainless steel beads for 25 seconds at setting of 30 (Qiagen Tissue Lyser). Samples were then homogenised for a further 2 min at setting of 10 to facilitate bacteria release from the tissue. Serial dilutions of homogenates were plated on BHI based agar plates supplemented amphotericin B (8 μg/mL), trimethoprim (5 μg/mL) and vancomycin (6 μg/mL), Nalidixic acid (10 μg/mL), polymyxin B (10 μg/mL) and bacitracin (200 μg/mL) (Dailidiene et al., (2006), *Appl Environ Microbiol.,* 72 (9), 5908-5914). Bacterial growth was determined 5-7 days post plating.

Sera were collected mice at different time points and assessed for the presence of urease specific IgG. Nunc 96 well maxisorb plates were coated with 10 μg/mL of Urease B protein (expressed from plasmid pILL927 and purified as described in reference Ferrero et al., (1994), *Infect. Immuno.,* 62(11), 4981-4989) in 100 μL carbonate buffer and incubated overnight at 4° C. Plates were washed 5× with PBS supplemented with 0.05% (v/v) Tween 20 (PBST) and then blocked with 200 μL of PBS supplemented with 2% BSA (w/v) for 2 hours at 37° C. Following 2× washes with PBST a 1:20 dilution mouse sera in 100 μL of PBST supplemented with 2% (w/v) BSA was added to duplicate wells and the plates incubated for 1 hour at room temperature. Subsequently, plates were washed with 5× with PBST and then a 1:1000 dilution of anti-mouse IgG alkaline phosphatase (Sigma Aldrich) in 100 μL PBST supplemented with 2% (w/v) was added to each well and the plates incubated at room temperature for 1 hour. After 5× washes with PEST, 200 μL of nitrophenyl phosphate substrate in diethanolamine buffer added to each well and the plates incubated for 40 min at room temperature in the dark before absorbance was measured at 405 nm.

*H. pylori* were harvested after growth for 24 h on BHI base agar plates and were rinsed in cold saline (0.9% v/v). The bacterial suspension was diluted to an $OD_{600}$ of 4 and 15 μL was added to 15 μL of saline supplemented with Tween 20 (0.2% v/v). To each sample 90 μL of KCl (200 mM; pH 3) was added and samples were incubated for 10 min while shaking at 300 rpm at room temperature. Subsequently the solution was neutralized by the addition of 120 μL of PBS (pH 6.8). 150 μL of each sample was added to 25 μL of phenol red sodium salt (80 mg/mL) and warmed to 37° C. The reaction was initiated by the addition of 75 μL of 0.5 M urea and the change in pH was measured by reading absorbance at 560 nm every 70 s.

Figure 3:
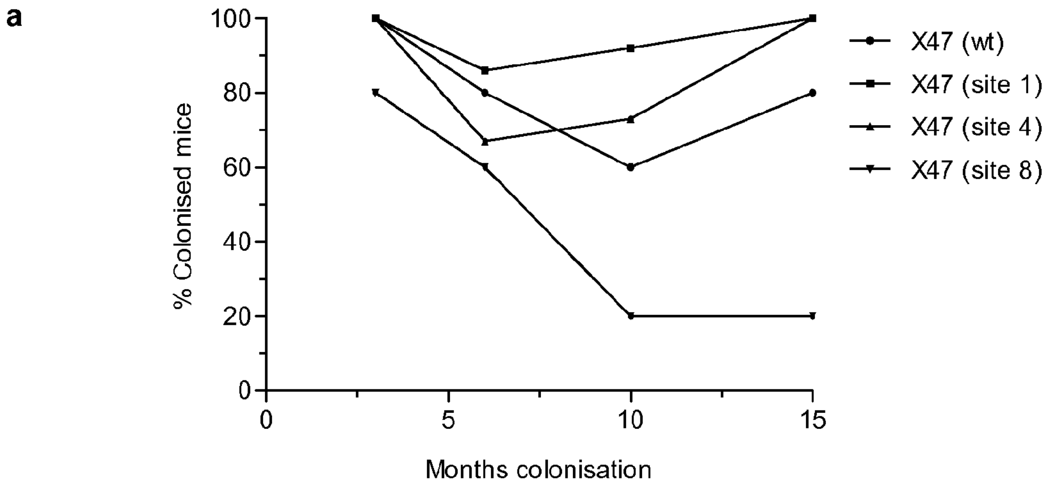
FIG. 3. Recombinant urease affects bacterial colonisation. a) Persistence over 15 months expressed as percentage of colonized (n=5-15). b) Colonisation level of mice infected with *H. pylori* expressing recombinant urease after 15 months (n=5; median displayed). c) Persistence of *H. pylori* expressing recombinant urease as indicated by anti-*H. pylori* IgG levels (n=12-20; median displayed). Strains were recombinant at either sites 1, 4 or 8 in urease. d) Comparison of anti-*H. pylori* IgG and anti-UreB IgG levels resulting from colonisation of mice for 3 months with X47 expressing wild-type urease, X47 (wt), or urease recombinant at site 8, X47 (site 8), (n=10-20; median displayed).
Figure 3:
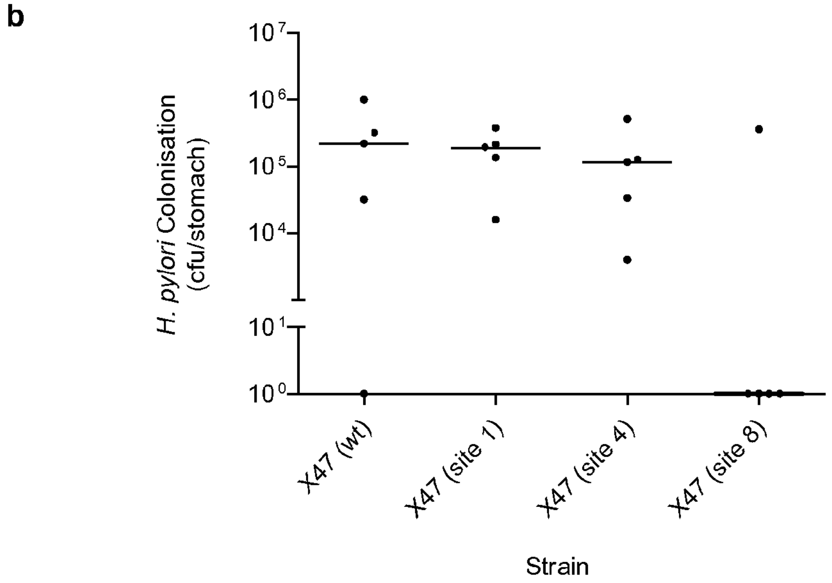
Figure 3:
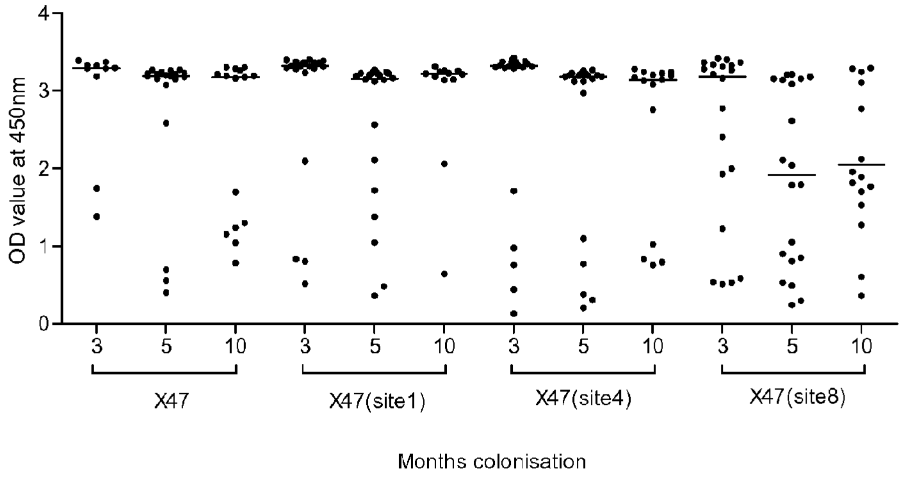
Figure 3:
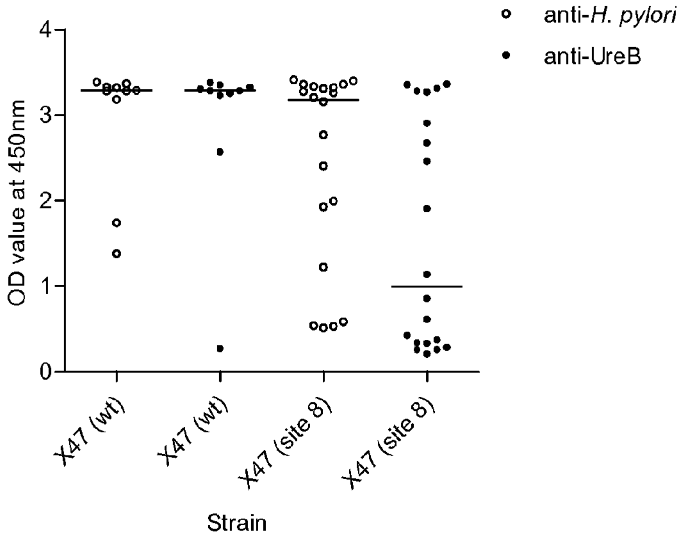
Figure 4:
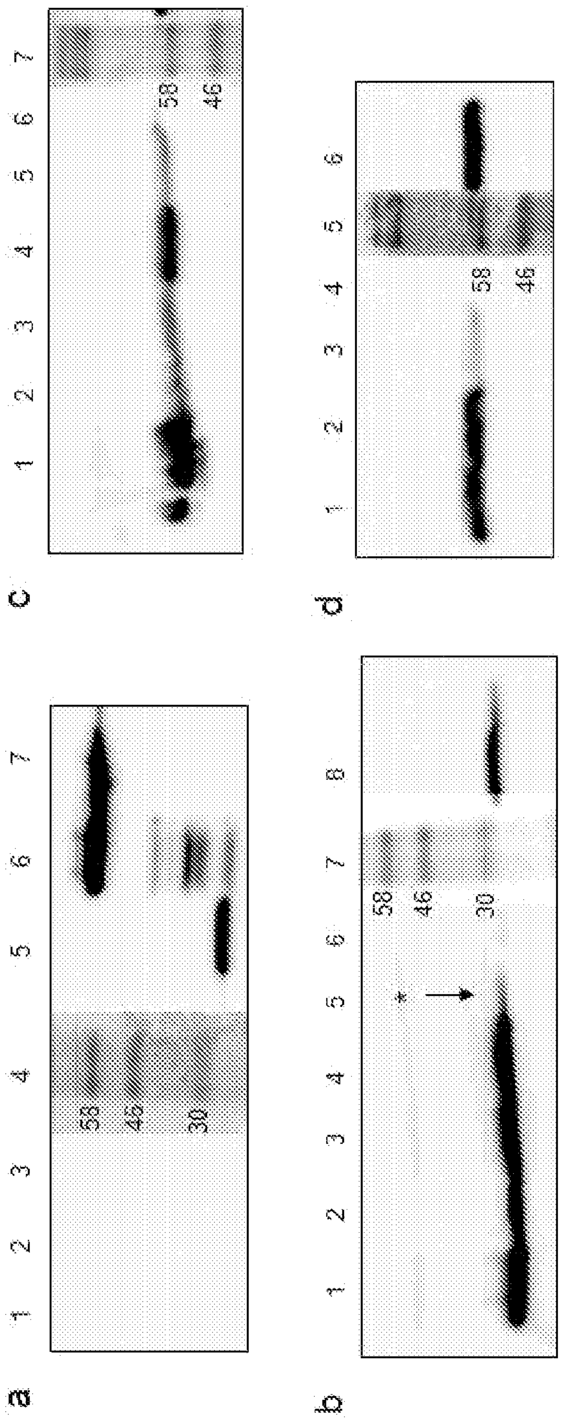
FIG. 4. Recombinant urease is stable in bacteria colonising mice. Western Blot analysis of *H. pylori* extracted from mice after 10 months colonisation, probed with anti-FLAG. Where described, each lane represents protein extracted from a pool of bacteria harvested from an individual mouse. a) lanes 1-3: pools of X47 (wt) from individual mice; lane 4: molecular size marker (MW: KDa shown); lane 5: X47 (site 1); lane 6: X47 (site 4); lane 7: X47 (site 8). b) lanes 1-5: pools of X47 (site 1) from individual mice; lane 7: molecular size marker; lane 8: X47 (site 1). c) lanes 1-5: pools of X47 (site 4) from individual mice; lane 7: molecular size marker. d) lanes 1-3: pools of X47 (site 8) from individual mice; lane 5: molecular size marker; lane 6: X47 (site 8). To confirm protein sample integrity urease expression was confirmed in wild-type X47 and a pool of X47 (site 1) from mice in which FLAG expression was not detected (annotated *; data not shown). Molecular of standard proteins (KDa) are shown directly adjacent to the marker.
Figure 5:
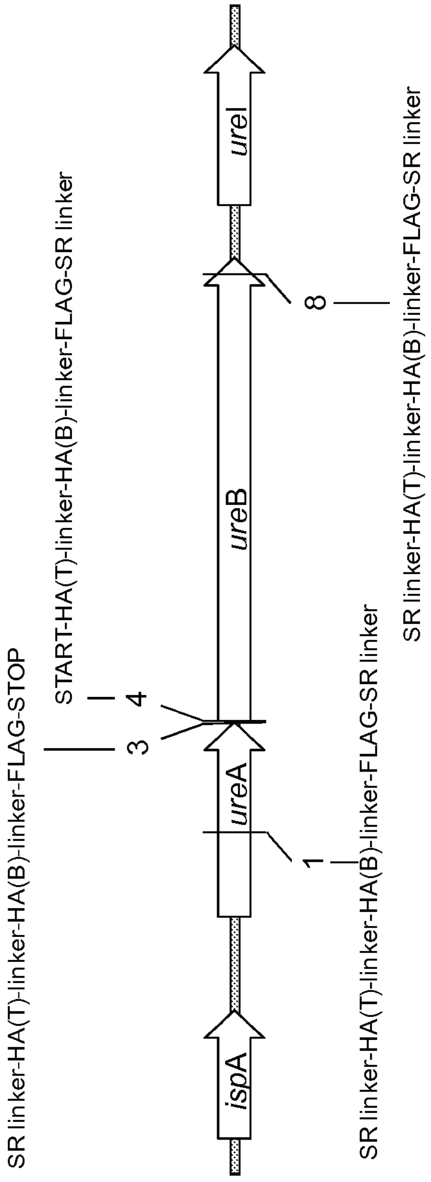
FIG. 5. A schematic showing insertion sites at the urease locus of DNA coding epitopes and linkers. Insertions were made in DNA corresponding to insertion after amino positions 102 (site 1) and 238 (site 3) of UreA (GenBank AAD07144.1; SEQ ID NO:3), and amino acid positions 1 (site 4) and 549 (site 8) of UreB (GenBank AAD07143.1 SEQ ID NO:1). Insertions at sites 3 and 4 correspond to the C and N terminals of UreA and UreB respectively. DNA coded HA(T): hemagglutinin T cell eptitope; HA(B) hemagglutinin B cell epitope; SR linker: semi-random linker; linker: GPSL linker; FLAG: FLAG epitope; STOP: STOP codon.

The ability of each mutant urease-producing *H. pylori* strain to colonise C57BL/6 mice was tested. The strain with site 3-mutant urease did not colonize mice (data not shown) and were not further studied, whereas each of the other three mutant strains colonized mice as efficiently as the wild-type in short-term (<3 months) infections. However, persistence of *H. pylori* with site 8-mutant urease was greatly reduced over longer periods of time (FIG. 3*a*). In confirmation, bacterial titers in mouse stomachs and anti-*H. pylori* IgG in serum were each much reduced relative to wild type and the other two mutants in the case of ten month infection by this strain (FIG. 3*b, c*). Important in our infection protocol, each inoculation used a pool of three independent transformant clones, which rules out concerns of possible attenuation by secondary mutations distinct from the insertions within urease. Further tests showed that nearly all bacteria recovered from mice 10 months after inoculation still expressed the expected mutant urease, thereby supporting the expectation that success in colonization was not due to loss of inserted DNAs. As the sole exception, just one mouse initially infected with the site 1 mutant strain seemed to produce revertant urease at ten months (FIG. 4). It was also striking that reduced urease activity measured in vitro did not correlate well with reduced colonisation ability, in that the site 1 mutant strain, whose urease was less acid stable than the others colonized mice as well as wild-type, and the site 8 mutant, whose urease activity was similar in acid resistance to that of wild type was nevertheless less persistent in mouse colonization. Rather, we propose an alternative role for the urease surface around site 8 (FIG. 1*a*), important during chronic infection.

In summary, a structure-based insertion mutagenesis of the urease complex identified two discrete regions on the enzyme surface that are needed for colonisation or persistence of *H. pylori*, site 3 and site 8 (FIG. 1*a*). The inability of recombinant *H. pylori* to colonise mice due to an insertion at site 3 gives further support for an alternative role of urease, different from acid neutralisation and warrants further investigation. In addition, our results suggest that the site 8 region is not essential for the de-acidification function of urease, but is rather involved in an alternative function required for persistence in the host. Site 8 is located in the turn of a beta-meander at the surface of the urease complex. No insertions or deletions are found at this site in homologous urease sequences in diverse organisms (Supplementary FIG. 2) and we therefore propose that the precise structure of this beta-meander is important for urease's alternative role during long-term colonisation. Sites 3 and −8 have in common that both are located in the proximity of the rotation axis that connects three alpha/beta trimers. Since enzymatic activity relies on the integrity of the alpha/beta trimer, the insertion of tags at sites 3 and −8 could modify the trimer/trimer interaction surface without compromising the enzymatic activity.

Adaptive immune responses change dramatically during the establishment and maintenance of chronic *H. pylori* infection, in particular at the site of infection. Urease site 8 overlaps with an established *H. pylori* $CD4^+$ T-cell epitope in response to which splenic lymphocytes produce cytokine IL-4 (Shi et al., (2007), *Vaccine,* 25(14), 2583-2590), a promoter of $Th_2$ responses and driver of antibody production, whereas sites 1, 3 and 4 do not coincide with any known B or T cell epitopes. We note that *H. pylori* expressing urease recombinant at site 8 infected animals at 3 months of infection, when their bacterial load is similar to that of bacteria expressing wild type urease (FIG. 3*a*), exhibit a weaker humoral response against the urease B subunit (UreB), but a normal response against total *H. pylori* antigen (FIG. 3*d*). Since urease constitutes up to 10% of bacterial protein (Marcus & Scott, (2001), *Helicobacter,* 6(2), 93-99; Hu & Mobley, (1990), *Infect Immun.,* 58(4), 992-998) the removal of an abundant $Th_2$ driver may prevent adequate immune modulation by *H. pylori* important in persistence and thereby facilitate bacterial clearance. Alternatively, given that binding of *H. pylori* to CD74 (MHC class II) on the gastric epithelium increases IL-8 secretion and up regulation of inflammatory cytokines (Beswick et al., (2006), *Infect Immun.,* 74(2), 1148-1155)) we can imagine direct interaction of the urease site 8 region with CD74-type host cell receptors affecting host cell signalling and thereby promoting chronic infection. This hypothesis is supported by the observation that CD74 receptors function as trimers (reviewed in Beswick et al. (2009), *World J. Gastroenterol.* 15:2855) and insertion of tags at sites 3 and −8 likely affect the trimerisation of alpha/beta trimers.

In conclusion, surface properties of the urease complex, distinct from urease activity per se, were found to be important for *H. pylori* colonisation and persistence. In the light of the many failed efforts to develop anti-*H. pylori* vaccines, a better molecular understanding of factors important in persistence should contribute to development of new, much needed therapeutic approaches.

The invention claimed is:

1. An isolated, genetically modified *Helicobacter pylori* comprising a functional urease comprising a modified UreB subunit, wherein the modified UreB subunit comprises the amino acid sequence of SEQ ID NO: 1, wherein at least ten additional contiguous amino acid residues have been inserted in a region between amino acid 549 and amino acid 550 of SEQ ID NO: 1, and wherein the modified *Helicobacter pylori* has a reduced ability to establish or maintain a persistent infection relative to a *H. pylori* expressing an unmodified urease.

2. An isolated, genetically modified *Helicobacter pylori* cell comprising a functional urease comprising a modified UreB subunit, wherein the modified UreB subunit comprises the amino acid sequence of SEQ ID NO: 1, wherein at least ten additional contiguous amino acid residues have been inserted in a region between amino acid 549 and amino acid 550 of SEQ ID NO: 1, and wherein the modified *Helicobacter pylori* has a reduced ability to establish or maintain a persistent infection relative to a *H. pylori* expressing an unmodified urease, said modified UreB subunit further comprising a deletion or substitution in a region between amino acid 529 and amino acid 555 of unmodified SEQ ID NO:1.

3. The isolated, genetically modified *Helicobacter pylori* cell of claim 2, wherein an amino acid residue selected from the group consisting of residue 547, residue 548, and residue 549 of unmodified SEQ ID NO:1 is substituted or deleted.

4. The isolated, genetically modified *Helicobacter pylori* of claim 3, wherein the substitution comprises a conservative or non-conservative amino acid change.

5. The isolated, genetically modified *Helicobacter pylori* of claim 1, wherein between 10 and 100 additional contiguous amino residues have been inserted in a region between amino acid 549 and amino acid 550 of SEQ ID NO:1.

6. The isolated, genetically modified *Helicobacter pylori* of claim 1, wherein the amino acid insertion is a heterologous antigen or a functional fragment thereof.

7. A method of producing a *Helicobacter pylori* having a reduced ability to establish or maintain a persistent infection, the method comprising:

inserting a nucleotide sequence encoding at least ten contiguous amino acid residues in-frame into a nucleic acid encoding a UreB subunit of a *H. pylori* urease to produce a recombinant UreB gene encoding a modified UreB subunit comprising the at least ten contiguous amino acid residues in a region of SEQ ID NO:1 between amino acid 549 and amino acid 550 of SEQ ID NO:1; and introducing the recombinant UreB gene into a *H. pylori* to produce a modified *H. pylori* expressing a functional urease protein comprising the modified UreB subunit, wherein said functional urease has a de-acidification function, and wherein the modified *H. pylori* has a reduced ability to establish or maintain a persistent infection relative to a *H. pylori* expressing an unmodified urease.

8. The method of claim 7, wherein the nucleotide sequence encoding at least ten contiguous amino acid residues encodes between 10 and 100 additional contiguous amino residues.

9. The isolated, genetically modified *Helicobacter pylori* of claim 2, wherein between 10 and 100 additional contiguous amino residues have been inserted in a region between amino acid 549 and amino acid 550 of SEQ ID NO:1.

10. The isolated, genetically modified *Helicobacter pylori* of claim 2, wherein the amino acid insertion is a heterologous antigen or a functional fragment thereof.

* * * * *

SEQUENCE LISTING

```
<160> NUMBER OF SEQ ID NOS: 71

<210> SEQ ID NO 1
<211> LENGTH: 569
<212> TYPE: PRT
<213> ORGANISM: Helicobacter pylori

<400> SEQUENCE: 1

Met Lys Lys Ile Ser Arg Lys Glu Tyr Val Ser Met Tyr Gly Pro Thr
1               5                   10                  15

Thr Gly Asp Lys Val Arg Leu Gly Asp Thr Asp Leu Ile Ala Glu Val
            20                  25                  30

Glu His Asp Tyr Thr Ile Tyr Gly Glu Glu Leu Lys Phe Gly Gly Gly
        35                  40                  45

Lys Thr Leu Arg Glu Gly Met Ser Gln Ser Asn Asn Pro Ser Lys Glu
    50                  55                  60

Glu Leu Asp Leu Ile Ile Thr Asn Ala Leu Ile Val Asp Tyr Thr Gly
65                  70                  75                  80

Ile Tyr Lys Ala Asp Ile Gly Ile Lys Asp Gly Lys Ile Ala Gly Ile
                85                  90                  95

Gly Lys Gly Gly Asn Lys Asp Met Gln Asp Gly Val Lys Asn Asn Leu
            100                 105                 110

Ser Val Gly Pro Ala Thr Glu Ala Leu Ala Gly Glu Gly Leu Ile Val
        115                 120                 125

Thr Ala Gly Gly Ile Asp Thr His Ile His Phe Ile Ser Pro Gln Gln
    130                 135                 140

Ile Pro Thr Ala Phe Ala Ser Gly Val Thr Thr Met Ile Gly Gly Gly
145                 150                 155                 160

Thr Gly Pro Ala Asp Gly Thr Asn Ala Thr Thr Ile Thr Pro Gly Arg
                165                 170                 175

Arg Asn Leu Lys Trp Met Leu Arg Ala Ala Glu Glu Tyr Ser Met Asn
            180                 185                 190

Leu Gly Phe Leu Ala Lys Gly Asn Ala Ser Asn Asp Ala Ser Leu Ala
        195                 200                 205

Asp Gln Ile Glu Ala Gly Ala Ile Gly Phe Lys Ile His Glu Asp Trp
    210                 215                 220
```

-continued

```
Gly Thr Thr Pro Ser Ala Ile Asn His Ala Leu Asp Val Ala Asp Lys
225                 230                 235                 240

Tyr Asp Val Gln Val Ala Ile His Thr Asp Thr Leu Asn Glu Ala Gly
                245                 250                 255

Cys Val Glu Asp Thr Met Ala Ala Ile Ala Gly Arg Thr Met His Thr
            260                 265                 270

Phe His Thr Glu Gly Ala Gly Gly Gly His Ala Pro Asp Ile Ile Lys
        275                 280                 285

Val Ala Gly Glu His Asn Ile Leu Pro Ala Ser Thr Asn Pro Thr Ile
    290                 295                 300

Pro Phe Thr Val Asn Thr Glu Ala Glu His Met Asp Met Leu Met Val
305                 310                 315                 320

Cys His His Leu Asp Lys Ser Ile Lys Glu Asp Val Gln Phe Ala Asp
                325                 330                 335

Ser Arg Ile Arg Pro Gln Thr Ile Ala Ala Glu Asp Thr Leu His Asp
            340                 345                 350

Met Gly Ile Phe Ser Ile Thr Ser Ser Asp Ser Gln Ala Met Gly Arg
        355                 360                 365

Val Gly Glu Val Ile Thr Arg Thr Trp Gln Thr Ala Asp Lys Asn Lys
    370                 375                 380

Lys Glu Phe Gly Arg Leu Lys Glu Glu Lys Gly Asp Asn Asp Asn Phe
385                 390                 395                 400

Arg Ile Lys Arg Tyr Leu Ser Lys Tyr Thr Ile Asn Pro Ala Ile Ala
                405                 410                 415

His Gly Ile Ser Glu Tyr Val Gly Ser Val Glu Val Gly Lys Val Ala
            420                 425                 430

Asp Leu Val Leu Trp Ser Pro Ala Phe Phe Gly Val Lys Pro Asn Met
        435                 440                 445

Ile Ile Lys Gly Gly Phe Ile Ala Leu Ser Gln Met Gly Asp Ala Asn
    450                 455                 460

Ala Ser Ile Pro Thr Pro Gln Pro Val Tyr Tyr Arg Glu Met Phe Ala
465                 470                 475                 480

His His Gly Lys Ala Lys Tyr Asp Ala Asn Ile Thr Phe Val Ser Gln
                485                 490                 495

Ala Ala Tyr Asp Lys Gly Ile Lys Glu Glu Leu Gly Leu Glu Arg Gln
            500                 505                 510

Val Leu Pro Val Lys Asn Cys Arg Asn Ile Thr Lys Lys Asp Met Gln
        515                 520                 525

Phe Asn Asp Thr Thr Ala His Ile Glu Val Asn Pro Glu Thr Tyr His
    530                 535                 540

Val Phe Val Asp Gly Lys Glu Val Thr Ser Lys Pro Ala Asn Lys Val
545                 550                 555                 560

Ser Leu Ala Gln Leu Phe Ser Ile Phe
                565
```

<210> SEQ ID NO 2
<211> LENGTH: 1707
<212> TYPE: DNA
<213> ORGANISM: Helicobacter pylori

<400> SEQUENCE: 2

```
atgaaaaaaa ttagccgcaa agaatatgtg agcatgtatg gcccgaccac cggcgataaa      60

gtgcgcctgg gcgataccga tctgattgcg gaagtggaac atgattatac catttatggc     120
```

-continued

```
gaagaactga aatttggcgg cggcaaaacc ctgcgcgaag gcatgagcca gagcaacaac    180

ccgagcaaag aagaactgga tctgattatt accaacgcgc tgattgtgga ttataccggc    240

atttataaag cggatattgg cattaaagat ggcaaaattg cgggcattgg caaaggcggc    300

aacaaagata tgcaggatgg cgtgaaaaac aacctgagcg tgggcccggc gaccgaagcg    360

ctggcgggcg aaggcctgat tgtgaccgcg ggcggcattg atacccatat tcattttatt    420

agcccgcagc agattccgac cgcgtttgcg agcggcgtga ccaccatgat tggcggcggc    480

accggcccgg cggatggcac caacgcgacc accattaccc cgggccgccg caacctgaaa    540

tggatgctgc gcgcggcgga agaatatagc atgaacctgg gctttctggc gaaaggcaac    600

gcgagcaacg atgcgagcct ggcggatcag attgaagcgg gcgcgattgg ctttaaaatt    660

catgaagatt ggggcaccac cccgagcgcg attaaccatg cgctggatgt ggcggataaa    720

tatgatgtgc aggtggcgat tcataccgat accctgaacg aagcgggctg cgtggaagat    780

accatggcgg cgattgcggg ccgcaccatg catacctttc ataccgaagg cgcgggcggc    840

ggccatgcgc cggatattat taaagtggcg ggcgaacata acattctgcc ggcgagcacc    900

aacccgacca ttccgtttac cgtgaacacc gaagcggaac atatggatat gctgatggtg    960

tgccatcatc tggataaaag cattaaagaa gatgtgcagt ttgcggatag ccgcattcgc   1020

ccgcagacca ttgcggcgga agataccctg catgatatgg gcatttttag cattaccagc   1080

agcgatagcc aggcgatggg ccgcgtgggc gaagtgatta cccgcacctg gcagaccgcg   1140

gataaaaaca aaaaagaatt tggccgcctg aaagaagaaa aaggcgataa cgataacttt   1200

cgcattaaac gctatctgag caaatatacc attaacccgg cgattgcgca tggcattagc   1260

gaatatgtgg gcagcgtgga agtgggcaaa gtggcggatc tggtgctgtg gagcccggcg   1320

ttttttggcg tgaaaccgaa catgattatt aaaggcggct ttattgcgct gagccagatg   1380

ggcgatgcga acgcgagcat tccgaccccg cagccggtgt attatcgcga aatgtttgcg   1440

catcatggca aagcgaaata tgatgcgaac attacctttg tgagccaggc ggcgtatgat   1500

aaaggcatta aagaagaact gggcctggaa cgccaggtgc tgccggtgaa aaactgccgc   1560

aacattacca aaaaagatat gcagtttaac gataccaccg cgcatattga agtgaacccg   1620

gaaacctatc atgtgtttgt ggatggcaaa gaagtgacca gcaaaccggc gaacaaagtg   1680

agcctggcgc agctgtttag catttt                                        1707
```

```
<210> SEQ ID NO 3
<211> LENGTH: 238
<212> TYPE: PRT
<213> ORGANISM: Helicobacter pylori

<400> SEQUENCE: 3

Met Lys Leu Thr Pro Lys Glu Leu Asp Lys Leu Met Leu His Tyr Ala
1               5                   10                  15

Gly Glu Leu Ala Lys Lys Arg Lys Glu Lys Gly Ile Lys Leu Asn Tyr
            20                  25                  30

Val Glu Ala Val Ala Leu Ile Ser Ala His Ile Met Glu Glu Ala Arg
        35                  40                  45

Ala Gly Lys Lys Thr Ala Ala Glu Leu Met Gln Glu Gly Arg Thr Leu
    50                  55                  60

Leu Lys Pro Asp Asp Val Met Asp Gly Val Ala Ser Met Ile His Glu
65                  70                  75                  80

Val Gly Ile Glu Ala Met Phe Pro Asp Gly Thr Lys Leu Val Thr Val
                85                  90                  95
```

His Thr Pro Ile Glu Ala Asn Gly Lys Leu Val Pro Gly Glu Leu Phe
            100                 105                 110

Leu Lys Asn Glu Asp Ile Thr Ile Asn Glu Gly Lys Lys Ala Val Ser
        115                 120                 125

Val Lys Val Lys Asn Val Gly Asp Arg Pro Val Gln Ile Gly Ser His
    130                 135                 140

Phe His Phe Phe Glu Val Asn Arg Cys Leu Asp Phe Asp Arg Glu Lys
145                 150                 155                 160

Thr Phe Gly Lys Arg Leu Asp Ile Ala Ser Gly Thr Ala Val Arg Phe
                165                 170                 175

Glu Pro Gly Glu Glu Lys Ser Val Glu Leu Ile Asp Ile Gly Gly Asn
            180                 185                 190

Arg Arg Ile Phe Gly Phe Asn Ala Leu Val Asp Arg Gln Ala Asp Asn
        195                 200                 205

Glu Ser Lys Lys Ile Ala Leu His Arg Ala Lys Glu Arg Gly Phe His
    210                 215                 220

Gly Ala Lys Ser Asp Asp Asn Tyr Val Lys Thr Ile Lys Glu
225                 230                 235

<210> SEQ ID NO 4
<211> LENGTH: 714
<212> TYPE: DNA
<213> ORGANISM: Helicobacter pylori

<400> SEQUENCE: 4
atgaaactga ccccgaaaga actggataaa ctgatgctgc attatgcggg cgaactggcg     60
aaaaaacgca aagaaaaagg cattaaactg aactatgtgg aagcggtggc gctgattagc    120
gcgcatatta tggaagaagc gcgcgcgggc aaaaaaaccg cggcggaact gatgcaggaa    180
ggccgcaccc tgctgaaacc ggatgatgtg atggatggcg tggcgagcat gattcatgaa    240
gtgggcattg aagcgatgtt tccggatggc accaaactgg tgaccgtgca taccccgatt    300
gaagcgaacg gcaaactggt gccgggcgaa ctgtttctga aaaacgaaga tattaccatt    360
aacgaaggca aaaaagcggt gagcgtgaaa gtgaaaaacg tgggcgatcg cccggtgcag    420
attggcagcc attttcattt ttttgaagtg aaccgctgcc tggattttga tcgcgaaaaa    480
acctttggca aacgcctgga tattgcgagc ggcaccgcgg tgcgctttga accgggcgaa    540
gaaaaaagcg tggaactgat tgatattggc ggcaaccgcc gcatttttgg ctttaacgcg    600
ctggtggatc gccaggcgga taacgaaagc aaaaaaattg cgctgcatcg cgcgaaagaa    660
cgcggctttc atggcgcgaa aagcgatgat aactatgtga aaaccattaa agaa          714

<210> SEQ ID NO 5
<211> LENGTH: 49
<212> TYPE: DNA
<213> ORGANISM: Helicobacter pylori

<400> SEQUENCE: 5
gtgtttaatc catagttata aagcatccca ttggcctcaa taggggtat                 49

<210> SEQ ID NO 6
<211> LENGTH: 48
<212> TYPE: DNA
<213> ORGANISM: Helicobacter pylori

<400> SEQUENCE: 6
ttcaatagct ataaattatt taataagtaa cggtggcggt aaaaccct                  48

-continued

<210> SEQ ID NO 7
<211> LENGTH: 52
<212> TYPE: DNA
<213> ORGANISM: Helicobacter pylori

<400> SEQUENCE: 7
ttcaatagct ataaattatt taataagtaa gtgagcttgg cgcaactctt ta 52

<210> SEQ ID NO 8
<211> LENGTH: 49
<212> TYPE: DNA
<213> ORGANISM: Helicobacter pylori

<400> SEQUENCE: 8
gtgtttaatc catagttata aagcatcgtg agcggtagtg tcgttgaat 49

<210> SEQ ID NO 9
<211> LENGTH: 27
<212> TYPE: DNA
<213> ORGANISM: Helicobacter pylori

<400> SEQUENCE: 9
gatgctttat aactatggat taaacac 27

<210> SEQ ID NO 10
<211> LENGTH: 30
<212> TYPE: DNA
<213> ORGANISM: Helicobacter pylori

<400> SEQUENCE: 10
ttacttatta aataatttat agctattgaa 30

<210> SEQ ID NO 11
<211> LENGTH: 81
<212> TYPE: DNA
<213> ORGANISM: Helicobacter pylori
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 11
ggcccttctt taggaaaaat ttcaaatctt tcaaagctvn nvnnvnnvnn vnnvnnggcc 60
tcaatagggg tatgcacggt t 81

<210> SEQ ID NO 12

<211> LENGTH: 82
<212> TYPE: DNA
<213> ORGANISM: Helicobacter pylori
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 12
ggcccttctt taggaaaaat ttcaaatctt tcaaagctvn nvnnvnnvnn vnnvnnctcc 60
ttaattgttt ttacatagtt gt 82

<210> SEQ ID NO 13
<211> LENGTH: 66
<212> TYPE: DNA
<213> ORGANISM: Helicobacter pylori

<400> SEQUENCE: 13
ggcccttctt taggaaaaat ttcaaatctt tcaaagctca tttcttactc cttaattgtt 60
tttaca 66

<210> SEQ ID NO 14
<211> LENGTH: 81
<212> TYPE: DNA
<213> ORGANISM: Helicobacter pylori
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 14
ggcccttctt taggaaaaat ttcaaatctt tcaaagctvn nvnnvnnvnn vnnvnngcca 60

```
tccacgaaca catggtaagt t                                              81


<210> SEQ ID NO 15
<211> LENGTH: 100
<212> TYPE: DNA
<213> ORGANISM: Helicobacter pylori

<400> SEQUENCE: 15

tttatcatcg tcatctttat aatctaagct aggcccagga tagctccctt ctttttcggt     60

taaccataag ctaggccctt ctttaggaaa aatttcaaat                         100


<210> SEQ ID NO 16
<211> LENGTH: 100
<212> TYPE: DNA
<213> ORGANISM: Helicobacter pylori

<400> SEQUENCE: 16

atttgaaatt tttcctaaag aagggcctag cttatggtta accgaaaaag aagggagcta     60

tcctgggcct agcttagatt ataaagatga cgatgataaa                         100


<210> SEQ ID NO 17
<211> LENGTH: 27
<212> TYPE: DNA
<213> ORGANISM: Helicobacter pylori

<400> SEQUENCE: 17

cgactttggt taacccgcaa atcccat                                        27


<210> SEQ ID NO 18
<211> LENGTH: 24
<212> TYPE: DNA
<213> ORGANISM: Helicobacter pylori

<400> SEQUENCE: 18

gggcgtggtg gattatgtgt atta                                           24


<210> SEQ ID NO 19
<211> LENGTH: 65
<212> TYPE: DNA
<213> ORGANISM: Helicobacter pylori
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 19
```

gattataaag atgacgatga taaannbnnb nnbnnbnnbn nbaatggtaa attagttcct 60
ggtga 65

<210> SEQ ID NO 20
<211> LENGTH: 65
<212> TYPE: DNA
<213> ORGANISM: Helicobacter pylori
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 20
tttatcatcg tcatctttat aatcvnnvnn vnnvnnvnnc tccttaattg tttttacata 60
gttgt 65

<210> SEQ ID NO 21
<211> LENGTH: 69
<212> TYPE: DNA
<213> ORGANISM: Helicobacter pylori
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 21
gattataaag atgacgatga taaannbnnb nnbnnbnnbn nbaaaaagat tagcagaaaa 60
gaatatgtt 69

<210> SEQ ID NO 22
<211> LENGTH: 67
<212> TYPE: DNA
<213> ORGANISM: Helicobacter pylori
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 22
gattataaag atgacgatga taaannbnnb nnbnnbnnbn nbaaagaagt aacttctaaa 60
ccagcca 67

<210> SEQ ID NO 23
<211> LENGTH: 34
<212> TYPE: PRT
<213> ORGANISM: Helicobacter pylori

<400> SEQUENCE: 23

Ile Glu Val Asn Pro Glu Thr Tyr His Val Phe Val Asp Gly Lys Glu
1 5 10 15

Val Thr Ser Lys Pro Ala Asn Lys Val Ser Leu Ala Gln Leu Phe Ser
20 25 30

Ile Phe

<210> SEQ ID NO 24
<211> LENGTH: 34
<212> TYPE: PRT
<213> ORGANISM: Helicobacter pylori

<400> SEQUENCE: 24

Ile Glu Val Asn Pro Glu Thr Tyr Lys Val Lys Val Asp Gly Asn Glu
1 5 10 15

Val Thr Ser His Ala Ala Asp Lys Leu Ser Leu Ala Gln Leu Tyr Asn
20 25 30

Leu Phe

<210> SEQ ID NO 25
<211> LENGTH: 34
<212> TYPE: PRT
<213> ORGANISM: Helicobacter pylori

<400> SEQUENCE: 25

Ile Glu Val Asn Pro Glu Thr Tyr Glu Val Arg Val Asn Asn Thr Lys
1 5 10 15

Ile Thr Ser Lys Pro Val Glu Lys Val Ser Leu Gly Gln Leu Tyr Cys
20 25 30

Leu Phe

<210> SEQ ID NO 26

-continued

<211> LENGTH: 34
<212> TYPE: PRT
<213> ORGANISM: Helicobacter pylori

<400> SEQUENCE: 26

Leu Thr Val Asp Pro Lys Ser Phe Glu Val Phe Leu Glu Gly Lys Leu
1 5 10 15

Cys Thr Ser Lys Pro Ala Ser Glu Leu Pro Leu Ala Gln Arg Tyr Thr
20 25 30

Phe Phe

<210> SEQ ID NO 27
<211> LENGTH: 34
<212> TYPE: PRT
<213> ORGANISM: Helicobacter pylori

<400> SEQUENCE: 27

Ile Glu Val Asp Pro Glu Thr Tyr Glu Val Lys Val Asp Gly Glu Ile
1 5 10 15

Ile Thr Cys Glu Pro Leu Lys Val Leu Pro Met Ala Gln Arg Tyr Phe
20 25 30

Leu Phe

<210> SEQ ID NO 28
<211> LENGTH: 34
<212> TYPE: PRT
<213> ORGANISM: Helicobacter pylori

<400> SEQUENCE: 28

Ile Glu Ile Asp Pro Glu Thr Tyr Glu Val Lys Val Asp Gly Glu Met
1 5 10 15

Ile Thr Cys Lys Pro Phe Glu Glu Val Ala Leu Ala Gln Arg Tyr Phe
20 25 30

Leu Phe

<210> SEQ ID NO 29
<211> LENGTH: 34
<212> TYPE: PRT
<213> ORGANISM: Helicobacter pylori

<400> SEQUENCE: 29

Ile Asp Val Asp Pro Gln Thr Tyr Glu Val Lys Val Asp Gly Gln Leu
1 5 10 15

Val Thr Cys Glu Pro Ala Glu Ile Val Pro Met Ala Gln Arg Tyr Phe
20 25 30

Leu Phe

<210> SEQ ID NO 30
<211> LENGTH: 34
<212> TYPE: PRT
<213> ORGANISM: Helicobacter pylori

<400> SEQUENCE: 30

Ile Thr Val Asn Pro Glu Asn Tyr Glu Val Arg Val Asp Gly Glu Lys
1 5 10 15

Ile Ile Cys Glu Pro Ala Thr His Leu Pro Met Ala Gln Arg Tyr Phe
20 25 30

Leu Phe

<210> SEQ ID NO 31
<211> LENGTH: 34
<212> TYPE: PRT
<213> ORGANISM: Helicobacter pylori

<400> SEQUENCE: 31

```
Ile Asp Val Asp Pro Gln Thr Tyr Glu Val Lys Val Asp Gly Arg Leu
1               5                   10                  15

Ile Thr Cys Glu Pro Ala Glu Val Val Ala Met Ala Gln Arg Tyr Phe
            20                  25                  30

Leu Phe
```

<210> SEQ ID NO 32
<211> LENGTH: 34
<212> TYPE: PRT
<213> ORGANISM: Helicobacter pylori

<400> SEQUENCE: 32

```
Ile Glu Val Asn Pro Gln Thr Tyr Glu Val Lys Ile Asn Gly Glu Leu
1               5                   10                  15

Ile Ser Ser Lys Ser Val Asp Ser Leu Ala Leu Ala Arg Lys Tyr Phe
            20                  25                  30

Met Ile
```

<210> SEQ ID NO 33
<211> LENGTH: 34
<212> TYPE: PRT
<213> ORGANISM: Helicobacter pylori

<400> SEQUENCE: 33

```
Leu Glu Val Asp Pro Gln Thr Tyr Glu Val Arg Ala Asp Gly Gln Leu
1               5                   10                  15

Leu Thr Cys Glu Pro Ala Glu Val Leu Pro Met Ala Gln Arg Tyr Phe
            20                  25                  30

Leu Phe
```

<210> SEQ ID NO 34
<211> LENGTH: 34
<212> TYPE: PRT
<213> ORGANISM: Helicobacter pylori

<400> SEQUENCE: 34

```
Ile Glu Val Asp Pro Gln Thr Tyr Glu Val Lys Val Asp Gly Lys Val
1               5                   10                  15

Ile Thr Cys Glu Ala Val Asp Val Leu Pro Met Ala Gln Arg Tyr Phe
            20                  25                  30

Leu Phe
```

<210> SEQ ID NO 35
<211> LENGTH: 34
<212> TYPE: PRT
<213> ORGANISM: Helicobacter pylori

<400> SEQUENCE: 35

```
Ile Glu Val Asn Pro Glu Thr Tyr Glu Val Arg Ala Asp Gly Glu Leu
1               5                   10                  15

Leu Thr Cys Glu Pro Ala Glu Val Leu Pro Met Ala Gln Arg Tyr Phe
            20                  25                  30

Leu Phe
```

<210> SEQ ID NO 36
<211> LENGTH: 34
<212> TYPE: PRT
<213> ORGANISM: Helicobacter pylori

<400> SEQUENCE: 36

```
Ile Glu Val Asp Pro Gln Thr Tyr Gln Val Lys Ala Asp Gly Gln Leu
1               5                   10                  15

Leu Trp Cys Glu Pro Ala Glu Val Leu Pro Leu Ala Gln Arg Tyr Phe
            20                  25                  30

Leu Phe
```

<210> SEQ ID NO 37
<211> LENGTH: 34
<212> TYPE: PRT
<213> ORGANISM: Helicobacter pylori

<400> SEQUENCE: 37

```
Met Glu Val Asp Pro Glu Thr Tyr His Val Arg Ala Asp Gly Glu Met
1               5                   10                  15

Leu Val Cys Glu Pro Ala Thr Val Leu Pro Met Ala Gln Arg Tyr Phe
            20                  25                  30

Leu Phe
```

<210> SEQ ID NO 38
<211> LENGTH: 34
<212> TYPE: PRT
<213> ORGANISM: Helicobacter pylori

<400> SEQUENCE: 38

```
Met Glu Val Asp Pro Glu Thr Tyr Glu Val Arg Ala Asp Gly Gln Leu
1               5                   10                  15

Leu Thr Cys Glu Pro Ala Glu Glu Leu Pro Met Ala Gln Arg Tyr Phe
            20                  25                  30

Leu Phe
```

<210> SEQ ID NO 39
<211> LENGTH: 34
<212> TYPE: PRT
<213> ORGANISM: Helicobacter pylori

<400> SEQUENCE: 39

```
Ile Glu Val Asp Pro Glu Thr Tyr Glu Val Arg Ala Asp Gly Glu Leu
1               5                   10                  15

Leu Thr Cys Glu Pro Ala Ser Val Leu Pro Met Ala Gln Arg Tyr Phe
            20                  25                  30

Leu Phe
```

<210> SEQ ID NO 40
<211> LENGTH: 34
<212> TYPE: PRT
<213> ORGANISM: Helicobacter pylori

<400> SEQUENCE: 40

```
Ile Ser Val Asp Pro Glu Thr Tyr Asp Val Val Ala Asp Gly Ala Leu
1               5                   10                  15

Leu Thr Cys Glu Pro Ala Ala Val Leu Pro Met Ala Gln Arg Tyr Phe
            20                  25                  30

Leu Phe
```

<210> SEQ ID NO 41
<211> LENGTH: 34
<212> TYPE: PRT
<213> ORGANISM: Helicobacter pylori

<400> SEQUENCE: 41

Ile Glu Val Asp Ala Gln Thr Tyr Glu Val Arg Ala Asp Gly Glu Leu
1 5 10 15

Leu Thr Cys Glu Pro Ala Thr Glu Leu Pro Leu Thr Gln Arg Tyr Cys
20 25 30

Leu Phe

<210> SEQ ID NO 42
<211> LENGTH: 34
<212> TYPE: PRT
<213> ORGANISM: Helicobacter pylori

<400> SEQUENCE: 42

Ile Thr Val Asp Pro Glu Thr Tyr Gln Val Ile Ala Asn Gly Glu Leu
1 5 10 15

Leu Thr Cys Glu Pro Ala Lys Val Leu Pro Met Ala Gln Arg Tyr Phe
20 25 30

Leu Phe

<210> SEQ ID NO 43
<211> LENGTH: 34
<212> TYPE: PRT
<213> ORGANISM: Helicobacter pylori

<400> SEQUENCE: 43

Ile Glu Val Asp Pro Glu Thr Tyr Glu Val Arg Ala Asp Gly Glu Leu
1 5 10 15

Leu Thr Cys Glu Pro Ala Thr Val Leu Pro Met Ala Gln Arg Tyr Phe
20 25 30

Leu Phe

<210> SEQ ID NO 44
<211> LENGTH: 34
<212> TYPE: PRT
<213> ORGANISM: Helicobacter pylori

<400> SEQUENCE: 44

Met Glu Val Asp Pro Glu Thr Tyr Glu Val Arg Ala Asp Gly Glu Leu
1 5 10 15

Leu Val Cys Glu Pro Ala Asp Val Leu Pro Met Ala Gln Arg Tyr Phe
20 25 30

Leu Phe

<210> SEQ ID NO 45
<211> LENGTH: 34
<212> TYPE: PRT
<213> ORGANISM: Helicobacter pylori

<400> SEQUENCE: 45

Ile Ser Val Asp Pro Glu Thr Tyr Gln Val Ile Ala Asp Gly Gln Leu
1 5 10 15

Leu Thr Cys Glu Pro Ala Lys Val Leu Pro Met Ala Gln Arg Tyr Phe
20 25 30

Leu Phe

<210> SEQ ID NO 46
<211> LENGTH: 34
<212> TYPE: PRT
<213> ORGANISM: Helicobacter pylori

<400> SEQUENCE: 46

Ile Glu Val Asp Pro Glu Thr Tyr Glu Val Arg Ala Asp Gly Glu Leu
1 5 10 15

Leu Thr Cys Glu Pro Ala Thr Val Leu Pro Leu Ala Gln Arg Tyr Phe
20 25 30

Leu Phe

<210> SEQ ID NO 47
<211> LENGTH: 34
<212> TYPE: PRT
<213> ORGANISM: Helicobacter pylori

<400> SEQUENCE: 47

Met Glu Val Asp Ser Gln Thr Tyr Glu Val Arg Ala Asn Gly Glu Leu
1 5 10 15

Leu Val Cys Glu Pro Ala Lys Val Leu Pro Leu Ala Gln Arg Tyr Phe
20 25 30

Leu Phe

<210> SEQ ID NO 48
<211> LENGTH: 34
<212> TYPE: PRT
<213> ORGANISM: Helicobacter pylori

<400> SEQUENCE: 48

Ile Glu Val Asn Pro Glu Thr Tyr Glu Val Arg Ala Asp Gly Glu Leu
1 5 10 15

Leu Thr Cys Gln Pro Ala Glu Val Leu Pro Met Ala Gln Arg Tyr Phe
20 25 30

Leu Phe

<210> SEQ ID NO 49
<211> LENGTH: 34
<212> TYPE: PRT
<213> ORGANISM: Helicobacter pylori

<400> SEQUENCE: 49

Ile Thr Val Asp Pro Gln Thr Tyr Glu Val Arg Ala Asp Gly Glu Leu
1 5 10 15

Leu Thr Cys Glu Pro Ala Glu Glu Leu Pro Leu Ala Gln Leu Tyr Thr
20 25 30

Leu Phe

<210> SEQ ID NO 50
<211> LENGTH: 34
<212> TYPE: PRT
<213> ORGANISM: Helicobacter pylori

<400> SEQUENCE: 50

Ile Glu Val Asn Pro Glu Thr Tyr Glu Val Arg Ala Asp Gly Glu Leu
1 5 10 15

Leu Thr Cys Gln Pro Ala Glu Val Leu Pro Met Ala Gln Arg Tyr Phe
20 25 30

Leu Phe

<210> SEQ ID NO 51
<211> LENGTH: 34
<212> TYPE: PRT
<213> ORGANISM: Helicobacter pylori

<400> SEQUENCE: 51

```
Ile Glu Val Asp Pro Gln Thr Tyr Glu Val Phe Ala Asn Gly Glu Leu
1               5                   10                  15

Leu Thr Cys Glu Pro Ala Glu Leu Leu Pro Leu Ala Gln Arg Tyr Leu
            20                  25                  30

Leu Leu
```

<210> SEQ ID NO 52
<211> LENGTH: 34
<212> TYPE: PRT
<213> ORGANISM: Helicobacter pylori

<400> SEQUENCE: 52

```
Val Thr Val Asp Pro Glu Thr Tyr Gln Val Val Ala Asp Gly Gln Leu
1               5                   10                  15

Leu Thr Cys Glu Pro Ala Thr Glu Leu Pro Met Ala Gln Arg Tyr Phe
            20                  25                  30

Leu Phe
```

<210> SEQ ID NO 53
<211> LENGTH: 34
<212> TYPE: PRT
<213> ORGANISM: Helicobacter pylori

<400> SEQUENCE: 53

```
Ile Thr Val Asp Pro Glu Thr Tyr Gln Val Val Ala Asp Gly Met Leu
1               5                   10                  15

Leu Thr Cys Glu Pro Ala Glu Val Leu Pro Met Ala Gln Arg Tyr Phe
            20                  25                  30

Leu Phe
```

<210> SEQ ID NO 54
<211> LENGTH: 34
<212> TYPE: PRT
<213> ORGANISM: Helicobacter pylori

<400> SEQUENCE: 54

```
Ile Glu Ile Asp Pro Lys Thr Tyr Gln Val Phe Ala Asp Gly Glu Glu
1               5                   10                  15

Leu Ser Cys Gln Pro Val Asp Tyr Val Pro Leu Gly Gln Arg Tyr Phe
            20                  25                  30

Leu Phe
```

<210> SEQ ID NO 55
<211> LENGTH: 34
<212> TYPE: PRT
<213> ORGANISM: Helicobacter pylori

<400> SEQUENCE: 55

```
Ile Asp Val Asp Pro Gln Thr Tyr Gln Val Lys Ala Asp Gly Val Leu
1               5                   10                  15

Leu Trp Cys Glu Pro Ala Glu Thr Leu Pro Met Ala Gln Arg Tyr Phe
```

20 25 30

Leu Phe

<210> SEQ ID NO 56
<211> LENGTH: 34
<212> TYPE: PRT
<213> ORGANISM: Helicobacter pylori

<400> SEQUENCE: 56

Met Glu Val Asp Pro Glu Thr Tyr Glu Val Arg Ala Asp Gly Arg Leu
1 5 10 15

Leu Thr Cys Glu Pro Ala Thr Val Leu Pro Leu Ala Gln Arg Tyr Phe
20 25 30

Leu Phe

<210> SEQ ID NO 57
<211> LENGTH: 34
<212> TYPE: PRT
<213> ORGANISM: Helicobacter pylori

<400> SEQUENCE: 57

Ile Ser Val Asp Pro Glu Thr Tyr Glu Val Phe Ser Asp Gly Glu Leu
1 5 10 15

Leu Thr Cys Glu Pro Leu Asn Glu Val Pro Met Ala Gln Arg Tyr Phe
20 25 30

Leu Leu

<210> SEQ ID NO 58
<211> LENGTH: 34
<212> TYPE: PRT
<213> ORGANISM: Helicobacter pylori

<400> SEQUENCE: 58

Leu Thr Val Asp Pro Glu Thr Tyr Glu Val Thr Val Asp Gly Glu Lys
1 5 10 15

Val Thr Cys Glu Pro Ala Glu Val Leu Ala Met Ala Gln Arg Tyr Phe
20 25 30

Leu Phe

<210> SEQ ID NO 59
<211> LENGTH: 34
<212> TYPE: PRT
<213> ORGANISM: Helicobacter pylori

<400> SEQUENCE: 59

Ile Glu Val Asp Ser Thr Tyr Glu Val Arg Ala Asp Gly Lys Gln Leu
1 5 10 15

Leu Val Cys Glu Pro Ala Thr Glu Leu Pro Met Ala Gln Arg Tyr Phe
20 25 30

Leu Phe

<210> SEQ ID NO 60
<211> LENGTH: 34
<212> TYPE: PRT
<213> ORGANISM: Helicobacter pylori

<400> SEQUENCE: 60

Ile Glu Ile Asp Tyr Lys Thr Phe Glu Val Phe Val Asn Gly Asn Lys
1 5 10 15

-continued

```
Ile Asn Val Pro Pro Ala Val Ser Leu Asn Met Thr Arg Arg Tyr Asn
            20                  25                  30

Leu Phe


<210> SEQ ID NO 61
<211> LENGTH: 34
<212> TYPE: PRT
<213> ORGANISM: Helicobacter pylori

<400> SEQUENCE: 61

Ile Gln Val Asp Pro Glu Thr Tyr Lys Val Thr Val Asp Gly Glu Asp
1               5                   10                  15

Val Thr Cys Glu Pro Ala Asp Val Leu Pro Met Ala Gln Arg Tyr Phe
            20                  25                  30

Leu Phe


<210> SEQ ID NO 62
<211> LENGTH: 34
<212> TYPE: PRT
<213> ORGANISM: Helicobacter pylori

<400> SEQUENCE: 62

Ile Thr Val Asp Pro Gln Thr Tyr Glu Val Phe Ala Asp Gly Val Leu
1               5                   10                  15

Leu Ser Cys Glu Pro Leu Glu Glu Val Pro Met Ala Gln Lys Tyr Phe
            20                  25                  30

Leu Leu


<210> SEQ ID NO 63
<211> LENGTH: 34
<212> TYPE: PRT
<213> ORGANISM: Helicobacter pylori

<400> SEQUENCE: 63

Ile Glu Val Asp Pro Glu Thr Tyr Ala Val Arg Ala Asp Gly Glu Leu
1               5                   10                  15

Leu Thr Cys Glu Pro Ala Thr Ser Leu Pro Leu Ala Gln Arg Tyr Phe
            20                  25                  30

Leu Phe


<210> SEQ ID NO 64
<211> LENGTH: 34
<212> TYPE: PRT
<213> ORGANISM: Helicobacter pylori

<400> SEQUENCE: 64

Ile Thr Val Asp Pro Gln Thr Tyr Asp Val Arg Val Asn Gly Glu Leu
1               5                   10                  15

Ile Thr Cys Glu Pro Ala Ala Glu Leu Pro Leu Ala Gln Arg Tyr Phe
            20                  25                  30

Leu Phe


<210> SEQ ID NO 65
<211> LENGTH: 34
<212> TYPE: PRT
<213> ORGANISM: Helicobacter pylori

<400> SEQUENCE: 65

Ile Thr Val Asp Pro Glu Thr Tyr Val Val Lys Ala Asp Gly Val His
1               5                   10                  15
```

Leu Val Cys Glu Pro Ala Thr Glu Leu Pro Leu Ala Gln Arg Tyr Phe
            20                  25                  30

Leu Phe

<210> SEQ ID NO 66
<211> LENGTH: 34
<212> TYPE: PRT
<213> ORGANISM: Helicobacter pylori

<400> SEQUENCE: 66

Ile Glu Val Asp Ser Glu Ser Tyr Glu Val Arg Ala Asp Gly Glu Leu
1               5                   10                  15

Leu Thr Cys Glu Pro Ala Thr Val Leu Pro Met Ala Gln Arg Tyr Phe
            20                  25                  30

Leu Phe

<210> SEQ ID NO 67
<211> LENGTH: 34
<212> TYPE: PRT
<213> ORGANISM: Helicobacter pylori

<400> SEQUENCE: 67

Ile Gln Val Asn Pro Glu Thr Tyr Glu Val Arg Val Asn Gly Glu Leu
1               5                   10                  15

Val Thr Cys Glu Pro Val Asp Glu Leu Pro Leu Ala Gln Lys Tyr Phe
            20                  25                  30

Leu Phe

<210> SEQ ID NO 68
<211> LENGTH: 34
<212> TYPE: PRT
<213> ORGANISM: Helicobacter pylori

<400> SEQUENCE: 68

Ile Glu Val Asp Pro Gln Asn Tyr Gln Val Arg Ala Asp Gly Gln Leu
1               5                   10                  15

Leu Trp Phe Glu Pro Ser Lys Val Leu Pro Met Ala Gln Arg Tyr Phe
            20                  25                  30

Leu Phe

<210> SEQ ID NO 69
<211> LENGTH: 34
<212> TYPE: PRT
<213> ORGANISM: Helicobacter pylori

<400> SEQUENCE: 69

Val Glu Val Asn Pro Glu Thr Tyr Glu Val Arg Ala Asn Gly Glu Leu
1               5                   10                  15

Leu Thr Cys Glu Pro Ala Thr Glu Leu Pro Met Ala Gln Arg Tyr Phe
            20                  25                  30

Leu Tyr

<210> SEQ ID NO 70
<211> LENGTH: 34
<212> TYPE: PRT
<213> ORGANISM: Helicobacter pylori

<400> SEQUENCE: 70

Ile Glu Val Asp Pro Glu Thr Tyr Glu Val Arg Ala Asp Gly Glu Leu

-continued

```
1               5                   10                  15

Leu Thr Cys Glu Pro Ala Thr Val Leu Pro Met Ala Gln Arg Tyr Phe
            20                  25                  30

Leu Phe


<210> SEQ ID NO 71
<211> LENGTH: 34
<212> TYPE: PRT
<213> ORGANISM: Helicobacter pylori

<400> SEQUENCE: 71

Val Glu Val Asp Pro Gln Thr Tyr Glu Val Phe Ala Asp Gly Asp Leu
1               5                   10                  15

Leu Thr Cys Asp Pro Ala Glu Glu Leu Pro Met Ala Gln Arg Tyr Leu
            20                  25                  30

Leu Leu
```